United States Patent
Fountaine

(10) Patent No.: US 11,607,182 B2
(45) Date of Patent: Mar. 21, 2023

(54) VOICE CONTROLLED ASSISTANCE FOR MONITORING ADVERSE EVENTS OF A USER AND/OR COORDINATING EMERGENCY ACTIONS SUCH AS CAREGIVER COMMUNICATION

(71) Applicant: LifePod Solutions, Inc., Boston, MA (US)

(72) Inventor: Dennis Fountaine, San Diego, CA (US)

(73) Assignee: LifePod Solutions, Inc., Cohasset, MA (US)

( * ) Notice: Subject to any disclaimer, the term of this patent is extended or adjusted under 35 U.S.C. 154(b) by 0 days.

(21) Appl. No.: 17/166,584

(22) Filed: Feb. 3, 2021

(65) Prior Publication Data
US 2021/0153818 A1    May 27, 2021

Related U.S. Application Data

(63) Continuation of application No. 17/095,224, filed on Nov. 11, 2020, now Pat. No. 11,020,064, which is a
(Continued)

(51) Int. Cl.
*A61B 5/00*       (2006.01)
*A61B 5/11*       (2006.01)
(Continued)

(52) U.S. Cl.
CPC ............ *A61B 5/747* (2013.01); *A61B 5/1113* (2013.01); *A61B 5/1117* (2013.01); *G06F 3/011* (2013.01);
(Continued)

(58) Field of Classification Search
CPC ... A61B 5/747; A61B 5/1113; G08B 21/0415; G08B 21/043; G08B 25/016; H04W 4/90
See application file for complete search history.

(56) References Cited

U.S. PATENT DOCUMENTS 5,086,391 A  *  2/1992  Chambers ............ A61B 5/0002
                                                340/539.18
5,612,869 A      3/1997  Letzt
                         (Continued)

FOREIGN PATENT DOCUMENTS

WO      2016/097368      6/2016

OTHER PUBLICATIONS

International Search Report and Written Opinion dated Aug. 9, 2018 in connection with International Application No. PCT/US2018/031783.

(Continued)

*Primary Examiner* — Daniel C Washburn
*Assistant Examiner* — Oluwadamilola M Ogunbiyi
(74) *Attorney, Agent, or Firm* — Wolf, Greenfield & Sacks, P.C.

(57) ABSTRACT

A user, such as an elderly person, may be assisted by an assistance device in his or her caregiving environment that operates in conjunction with one or more server computers. The assistance device may execute a schedule of assistance actions where each assistance action is associated with a time and is executed at that time to assist the user. An assistance action may present an input request to a user, process a voice input of the user, and analyze the voice input to determine that the voice input corresponds to a negative response event, a positive response event, or a non-response event. Based on the categorization of one or more voice inputs as negative response events, positive response events, or non-response events, it may be determined to notify a caregiver of the user, for example where the user has not responded to a number of assistance actions.

20 Claims, 23 Drawing Sheets

MONITORING AND ASSISTANCE
PROCESS FLOW

Related U.S. Application Data continuation of application No. 16/936,019, filed on Jul. 22, 2020, which is a continuation of application No. 15/802,705, filed on Nov. 3, 2017, now Pat. No. 10,722,185, which is a continuation of application No. 15/590,012, filed on May 9, 2017, now Pat. No. 10,258,295.

(51) Int. Cl.

| | | |
|---|---|---|
| *G06F 3/01* | (2006.01) | |
| *G06F 3/16* | (2006.01) | |
| *G06Q 50/22* | (2018.01) | |
| *G08B 21/04* | (2006.01) | |
| *G08B 25/01* | (2006.01) | |
| *G10L 15/18* | (2013.01) | |
| *G10L 15/22* | (2006.01) | |
| *G10L 25/63* | (2013.01) | |
| *G10L 25/66* | (2013.01) | |
| *G16H 40/67* | (2018.01) | |
| *G08B 7/06* | (2006.01) | |
| *G08B 17/10* | (2006.01) | |
| *G10L 15/08* | (2006.01) | |
| *H04N 21/2187* | (2011.01) | |
| *H04W 4/90* | (2018.01) | |
| *G10L 15/26* | (2006.01) | |

(52) U.S. Cl.
CPC ............ *G06F 3/167* (2013.01); *G06Q 50/22* (2013.01); *G08B 21/043* (2013.01); *G08B 21/0407* (2013.01); *G08B 21/0415* (2013.01); *G08B 21/0423* (2013.01); *G08B 21/0446* (2013.01); *G08B 21/0469* (2013.01); *G08B 25/016* (2013.01); *G10L 15/1822* (2013.01); *G10L 15/22* (2013.01); *G10L 15/26* (2013.01); *G10L 25/63* (2013.01); *G10L 25/66* (2013.01); *G16H 40/67* (2018.01); *H04N 21/2187* (2013.01); *H04W 4/90* (2018.02); *A61B 2560/0242* (2013.01); *G08B 7/066* (2013.01); *G08B 17/10* (2013.01); *G10L 2015/088* (2013.01)

(56) References Cited

U.S. PATENT DOCUMENTS

| | | | |
|---|---|---|---|
| 5,625,864 A | 4/1997 | Budow | |
| 6,091,362 A * | 7/2000 | Stilp | G01S 5/0215 |
| | | | 342/465 |
| 6,335,927 B1 | 1/2002 | Elliot et al. | |
| 7,412,260 B2 | 8/2008 | Gailey et al. | |
| 7,827,040 B2 | 11/2010 | Brown | |
| 8,311,863 B1 * | 11/2012 | Kemp | G06Q 10/0639 |
| | | | 705/7.11 |
| 9,363,656 B1 * | 6/2016 | George | H04W 4/90 |
| 9,503,873 B1 * | 11/2016 | Yadav | H04W 4/08 |
| 9,715,814 B2 | 7/2017 | Sattari | |
| 9,786,148 B2 | 10/2017 | Sundaram | |
| 9,852,599 B1 * | 12/2017 | Slavin | G08B 21/043 |
| 9,918,212 B1 * | 3/2018 | Immendorf | H04W 4/021 |
| 10,157,042 B1 | 12/2018 | Jayakumar et al. | |
| 10,258,295 B2 | 4/2019 | Fountaine | |
| 10,311,707 B2 | 6/2019 | Halverson | |
| 10,412,206 B1 | 9/2019 | Liang et al. | |
| 10,572,107 B1 | 2/2020 | Beebe et al. | |
| 10,658,074 B1 | 5/2020 | Sorkey et al. | |
| 10,722,185 B2 | 7/2020 | Fountaine | |
| 11,020,064 B2 | 6/2021 | Fountaine | |
| 2001/0054085 A1 | 12/2001 | Kurganov | |
| 2002/0026266 A1 * | 2/2002 | Montague | G08B 25/006 |
| | | | 701/1 |
| 2002/0150227 A1 | 10/2002 | Abraham | |
| 2003/0052787 A1 | 3/2003 | Zerhusen et al. | |
| 2004/0143602 A1 * | 7/2004 | Ruiz | H04N 7/181 |
| 2005/0075542 A1 | 4/2005 | Goldreich | |
| 2005/0240571 A1 | 10/2005 | Haigh et al. | |
| 2005/0288721 A1 | 12/2005 | Girouard et al. | |
| 2006/0049936 A1 | 3/2006 | Collins, Jr. et al. | |
| 2006/0143050 A1 | 6/2006 | Dean | |
| 2006/0288225 A1 | 12/2006 | Jung et al. | |
| 2007/0037605 A1 | 2/2007 | Logan | |
| 2007/0066276 A1 * | 3/2007 | Kuz | H04M 3/5116 |
| | | | 455/404.1 |
| 2007/0189128 A1 | 8/2007 | Chung | |
| 2007/0253021 A1 | 11/2007 | Mehta et al. | |
| 2007/0255599 A1 | 11/2007 | Henry | |
| 2008/0165286 A1 | 7/2008 | Oh et al. | |
| 2008/0247519 A1 | 10/2008 | Abella et al. | |
| 2008/0294462 A1 | 11/2008 | Nuhaan et al. | |
| 2009/0177641 A1 | 7/2009 | Raghavan | |
| 2009/0243833 A1 | 10/2009 | Huang et al. | |
| 2009/0259728 A1 | 10/2009 | Berisford et al. | |
| 2010/0131280 A1 | 5/2010 | Bogineni | |
| 2010/0257458 A1 | 10/2010 | Herlein et al. | |
| 2010/0269049 A1 | 10/2010 | Fearin | |
| 2010/0295684 A1 | 11/2010 | Hsieh et al. | |
| 2011/0059748 A1 * | 3/2011 | Taylor | H04W 4/021 |
| | | | 370/328 |
| 2011/0123971 A1 | 5/2011 | Berkowitz et al. | |
| 2011/0282671 A1 | 11/2011 | Dicks et al. | |
| 2011/0301440 A1 | 12/2011 | Riley et al. | |
| 2012/0087482 A1 * | 4/2012 | Alexander, Sr. | G08B 25/009 |
| | | | 379/45 |
| 2012/0166322 A1 | 6/2012 | Simon | |
| 2012/0196571 A1 | 8/2012 | Grkov et al. | |
| 2013/0077536 A1 * | 3/2013 | Piett | H04W 4/025 |
| | | | 370/259 |
| 2013/0147899 A1 | 6/2013 | Labhard | |
| 2013/0149987 A1 * | 6/2013 | Cheng | H04L 67/1002 |
| | | | 455/404.1 |
| 2013/0150686 A1 * | 6/2013 | Fronterhouse | G16H 40/67 |
| | | | 600/323 |
| 2013/0173305 A1 | 7/2013 | Hyde et al. | |
| 2013/0253950 A1 | 9/2013 | Vanderpohl, III et al. | |
| 2013/0267795 A1 | 10/2013 | Cosentino et al. | |
| 2014/0004490 A1 | 1/2014 | Welling et al. | |
| 2014/0019157 A1 * | 1/2014 | Nudd | G16H 40/67 |
| | | | 705/2 |
| 2014/0073880 A1 | 3/2014 | Boucher et al. | |
| 2014/0168453 A1 | 6/2014 | Shoemake et al. | |
| 2014/0214426 A1 | 7/2014 | Kanevsky et al. | |
| 2014/0259017 A1 | 9/2014 | Murray et al. | |
| 2014/0351411 A1 * | 11/2014 | Woods | H04W 4/021 |
| | | | 709/224 |
| 2015/0002292 A1 * | 1/2015 | Cavalcanti | G08B 21/0275 |
| | | | 340/539.12 |
| 2015/0019255 A1 | 1/2015 | Coetzer | |
| 2015/0094830 A1 | 4/2015 | Lipoma et al. | |
| 2015/0116107 A1 | 4/2015 | Fadell et al. | |
| 2015/0185752 A1 | 7/2015 | Bard et al. | |
| 2015/0193450 A1 | 7/2015 | Chung | |
| 2015/0269827 A1 | 9/2015 | Hopkins et al. | |
| 2015/0295784 A1 | 10/2015 | Kim et al. | |
| 2015/0302766 A1 | 10/2015 | Oberlander et al. | |
| 2015/0373183 A1 | 12/2015 | Woolsey et al. | |
| 2016/0041811 A1 | 2/2016 | Parundekar et al. | |
| 2016/0052391 A1 | 2/2016 | Walsh et al. | |
| 2016/0057595 A1 * | 2/2016 | Ahmed | H04W 4/02 |
| | | | 455/404.1 |
| 2016/0066189 A1 | 3/2016 | Mahaffey et al. | |
| 2016/0088455 A1 * | 3/2016 | Bozik | H04L 41/0654 |
| | | | 370/259 |
| 2016/0106627 A1 | 4/2016 | Geman et al. | |
| 2016/0179787 A1 | 6/2016 | Deleeuw | |
| 2016/0232302 A1 | 8/2016 | Geronimo-Button | |
| 2016/0232773 A1 * | 8/2016 | Abeyta | H04L 12/1895 |
| 2016/0324460 A1 | 11/2016 | Kusens | |
| 2016/0329872 A1 | 11/2016 | Dizon | |
| 2017/0094490 A1 * | 3/2017 | Ryan | H04W 4/90 |
| 2017/0103754 A1 | 4/2017 | Higbie et al. | |

(56) References Cited

U.S. PATENT DOCUMENTS

| | | | |
|---|---|---|---|
| 2017/0123391 A1* | 5/2017 | Sinha | G05B 15/02 |
| 2017/0124279 A1 | 5/2017 | Rothman | |
| 2017/0140629 A1* | 5/2017 | Briggs | G08B 21/043 |
| 2017/0140754 A1 | 5/2017 | Ichimura | |
| 2017/0160813 A1 | 6/2017 | Divakaran et al. | |
| 2017/0186301 A1 | 6/2017 | Vaddepally et al. | |
| 2017/0206899 A1 | 7/2017 | Bryant et al. | |
| 2017/0213191 A1 | 7/2017 | Pitcher | |
| 2017/0221283 A1* | 8/2017 | Pal | B60R 25/24 |
| 2017/0239432 A1 | 8/2017 | Delangre et al. | |
| 2017/0251347 A1* | 8/2017 | Mehta | H04W 4/90 |
| 2017/0296107 A1 | 10/2017 | Reid et al. | |
| 2018/0004909 A1 | 1/2018 | Cronin et al. | |
| 2018/0007201 A1 | 1/2018 | Kurganov | |
| 2018/0032692 A1 | 2/2018 | Hickle et al. | |
| 2018/0047391 A1 | 2/2018 | Baik et al. | |
| 2018/0054506 A1 | 2/2018 | Hart et al. | |
| 2018/0060492 A1 | 3/2018 | Feng et al. | |
| 2018/0060495 A1 | 3/2018 | Mahapatra et al. | |
| 2018/0075219 A1 | 3/2018 | Klein et al. | |
| 2018/0096690 A1 | 4/2018 | Mixter et al. | |
| 2018/0122378 A1 | 5/2018 | Mixter et al. | |
| 2018/0144590 A1 | 5/2018 | Mixter et al. | |
| 2018/0190264 A1 | 7/2018 | Mixter et al. | |
| 2018/0210701 A1 | 7/2018 | Segal et al. | |
| 2018/0217264 A1 | 8/2018 | Syrjärinne | |
| 2018/0226158 A1 | 8/2018 | Fish et al. | |
| 2018/0268346 A1 | 9/2018 | Cronin et al. | |
| 2018/0310159 A1* | 10/2018 | Katz | H04M 3/4217 |
| 2018/0315488 A1 | 11/2018 | Miranda et al. | |
| 2018/0325469 A1 | 11/2018 | Fountaine | |
| 2018/0325470 A1 | 11/2018 | Fountaine | |
| 2019/0132932 A1 | 5/2019 | Klecha et al. | |
| 2019/0179607 A1 | 6/2019 | Thangarathnam et al. | |
| 2019/0228631 A1 | 7/2019 | Stinson et al. | |
| 2019/0233870 A1 | 8/2019 | Buck et al. | |
| 2019/0290129 A1 | 9/2019 | Hanina et al. | |
| 2019/0343456 A1 | 11/2019 | Kahlert et al. | |
| 2019/0364505 A1* | 11/2019 | Wang | H04W 52/0235 |
| 2019/0378518 A1 | 12/2019 | Jeong et al. | |
| 2020/0047341 A1 | 2/2020 | Song et al. | |
| 2020/0066254 A1 | 2/2020 | Hiroe et al. | |
| 2020/0114159 A1 | 4/2020 | Kaib et al. | |
| 2020/0265699 A1* | 8/2020 | Bango | G08B 7/06 |
| 2020/0286620 A1 | 9/2020 | Fallon et al. | |
| 2020/0327989 A1 | 10/2020 | Kuenen et al. | |
| 2021/0038170 A1 | 2/2021 | Fountaine | |
| 2021/0077036 A1 | 3/2021 | Fountaine | |
| 2021/0104304 A1 | 4/2021 | Davidovics et al. | |
| 2021/0142798 A1 | 5/2021 | Pulicharla et al. | |
| 2021/0196209 A1 | 7/2021 | Fountaine | |
| 2021/0375272 A1 | 12/2021 | Madwed et al. | |

OTHER PUBLICATIONS

International Preliminary Report on Patentability dated Nov. 21, 2019 in connection with International Application No. PCT/US2018/031783.
U.S. Appl. No. 16/936,019, filed Jul. 22, 2020, Fountaine.
U.S. Appl. No. 17/095,224, filed Nov. 11, 2020, Fountaine.
PCT/US2018/031783, dated Aug. 9, 2018, International Search Report and Written Opinion.
PCT/US2018/031783, dated Nov. 21, 2019, International Preliminary Report on Patentability.

* cited by examiner

*FIG. 13*  MONITORING AND ASSISTANCE PROCESS FLOW

FIG. 14  ADVERSE EVENT DETERMINATION PROCESS FLOW

*FIG. 15*   EMERGENCY ACTION PROCESS FLOW

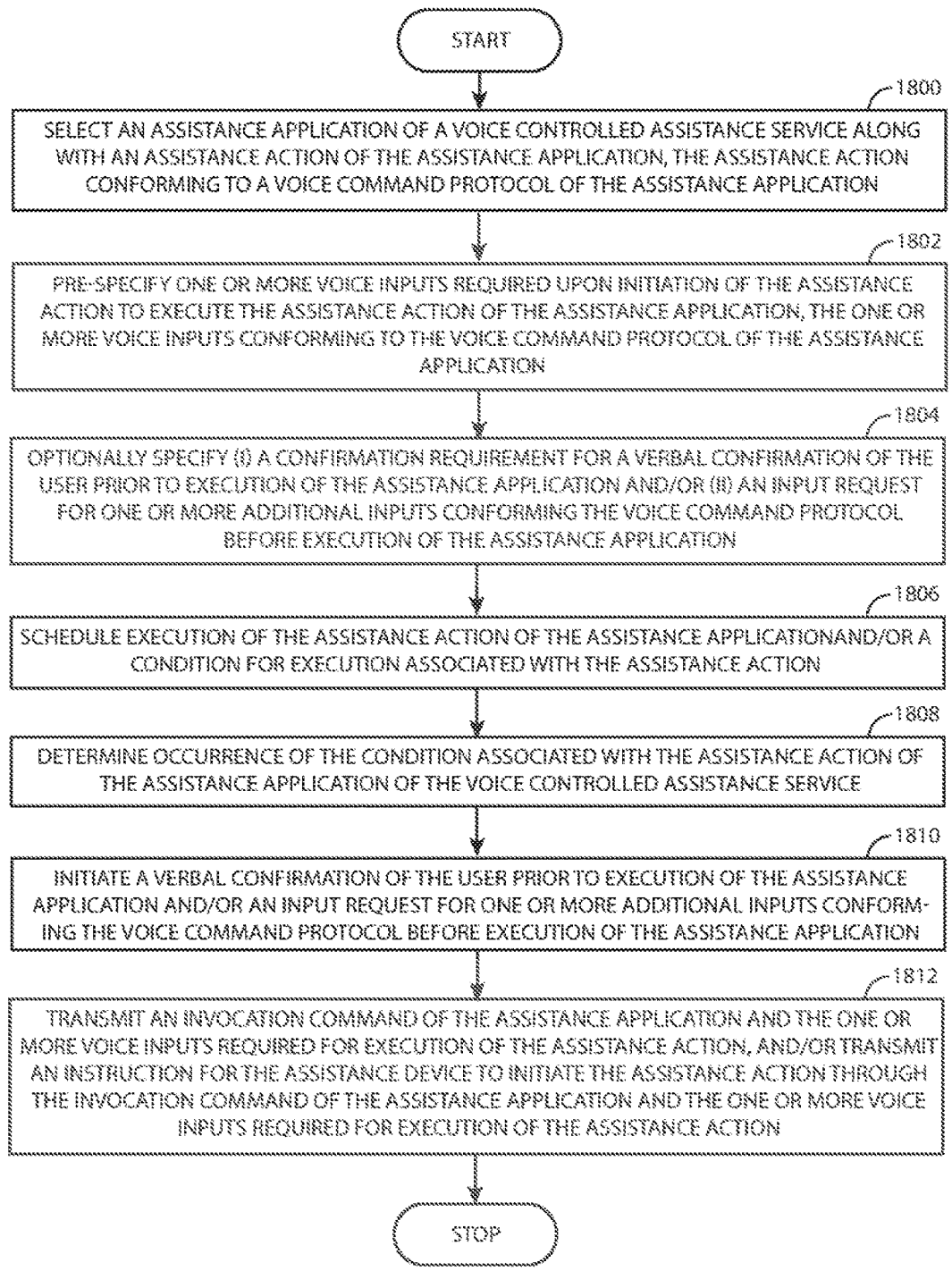
FIG. 18  APPLICATION ASSISTANCE AUTOMATION PROCESS FLOW

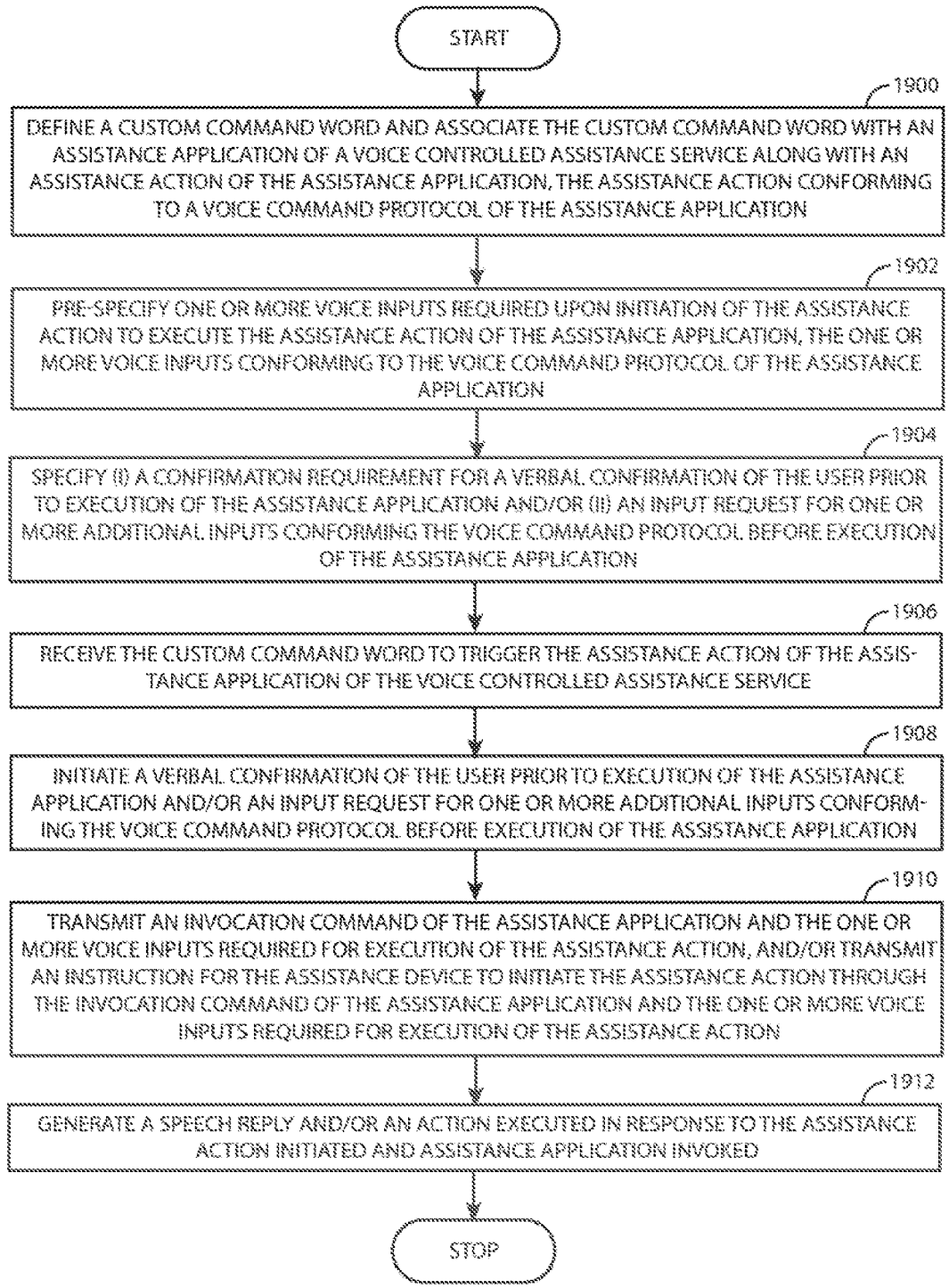
*FIG. 19*  CUSTOMIZABLE COMMAND PROCESS FLOW

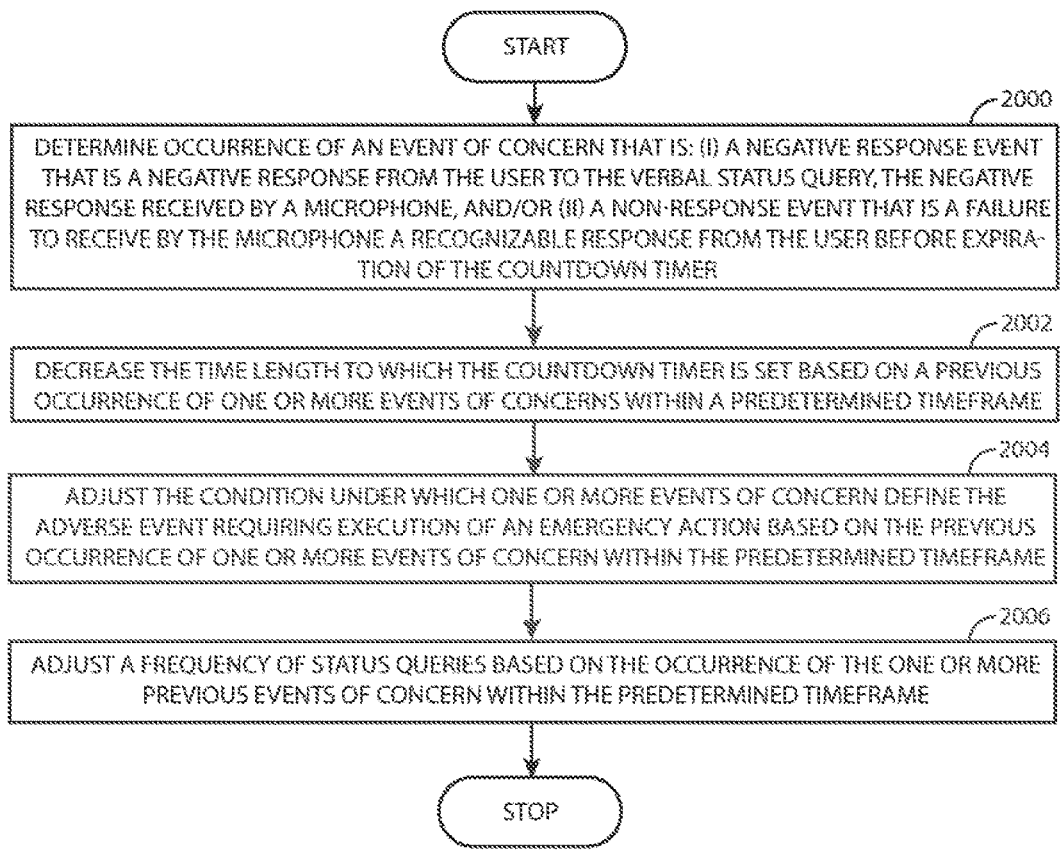
FIG. 20  ADVERSE EVENT CALIBRATION PROCESS FLOW

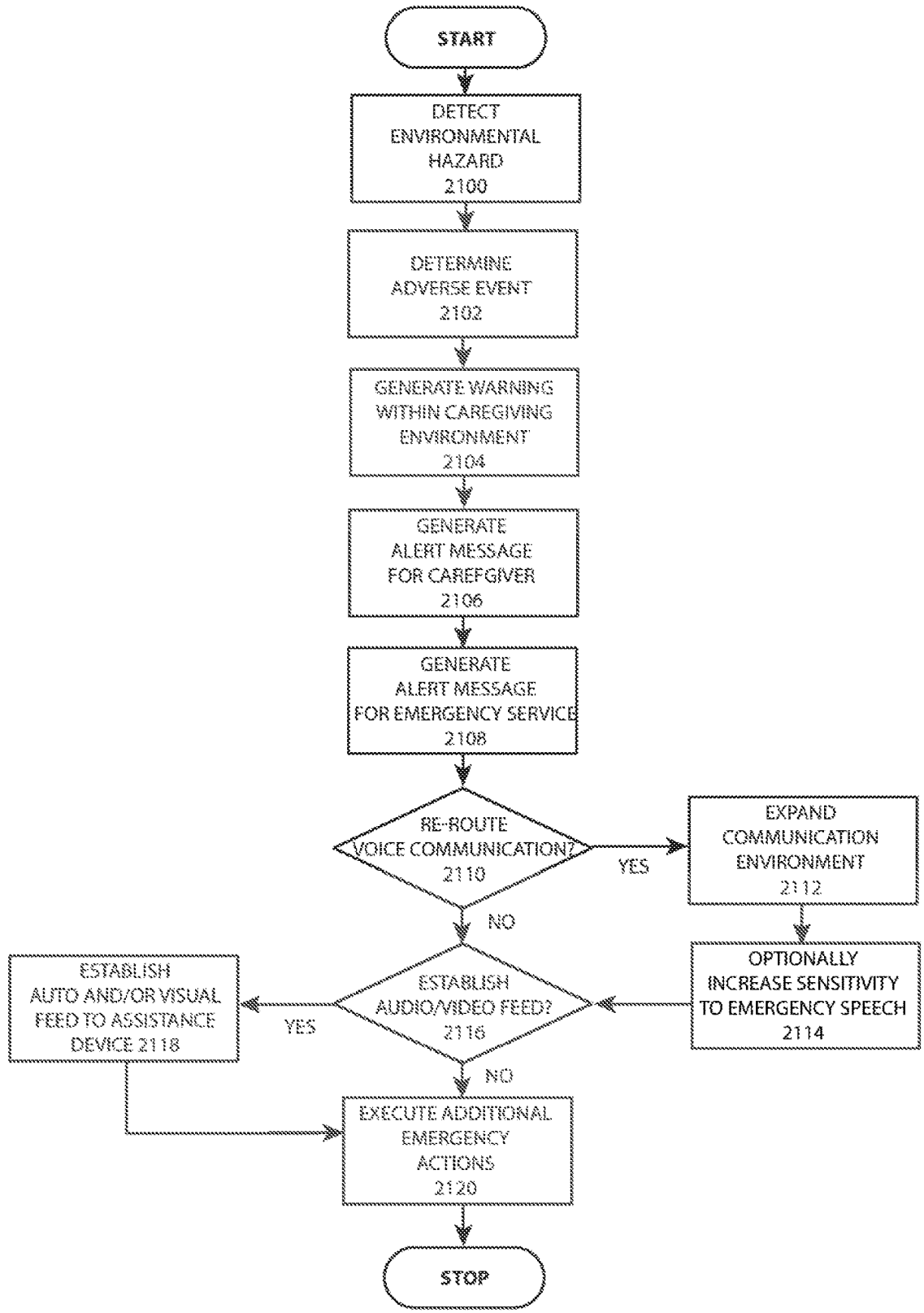
FIG. 21  PERSONAL VITALS / ENVIRONMENTAL HAZARD ACTION PROCESS FLOW

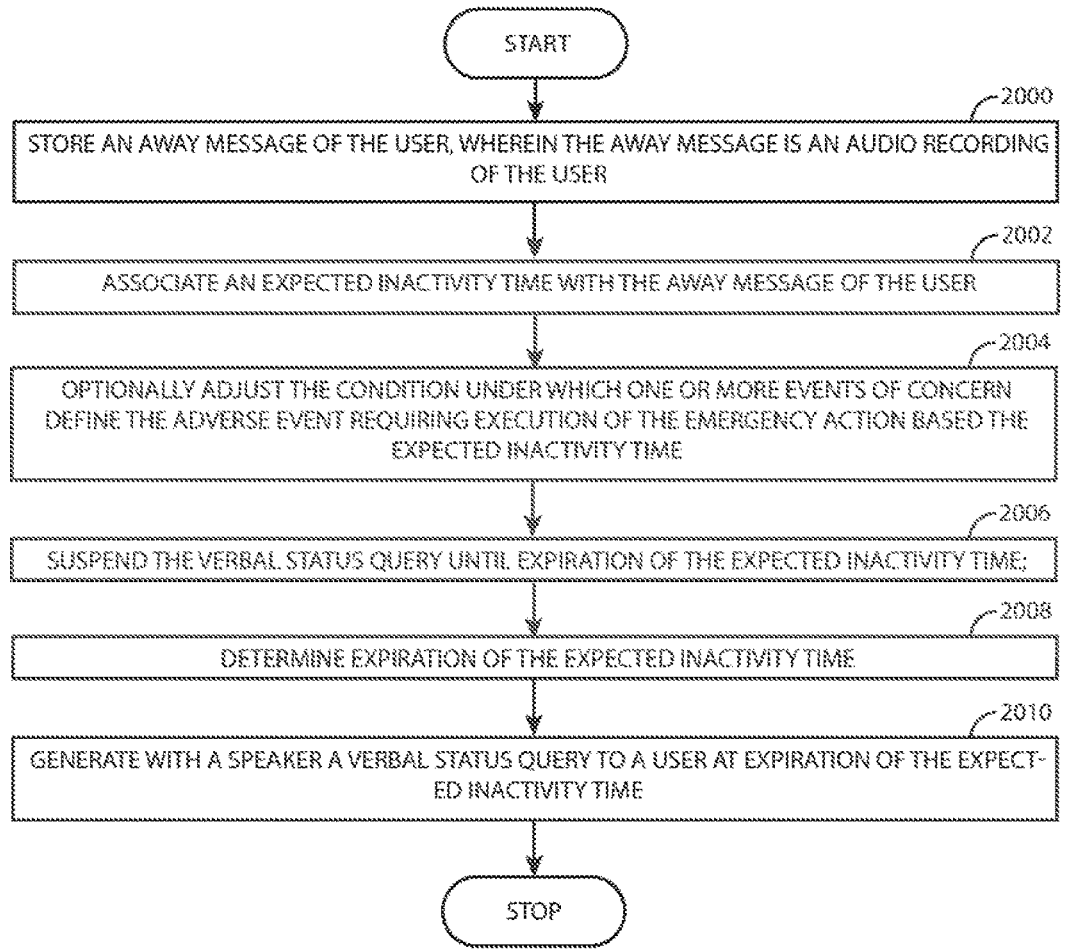
FIG. 22 USER MESSAGE / QUERY SUSPENSION PROCESS FLOW

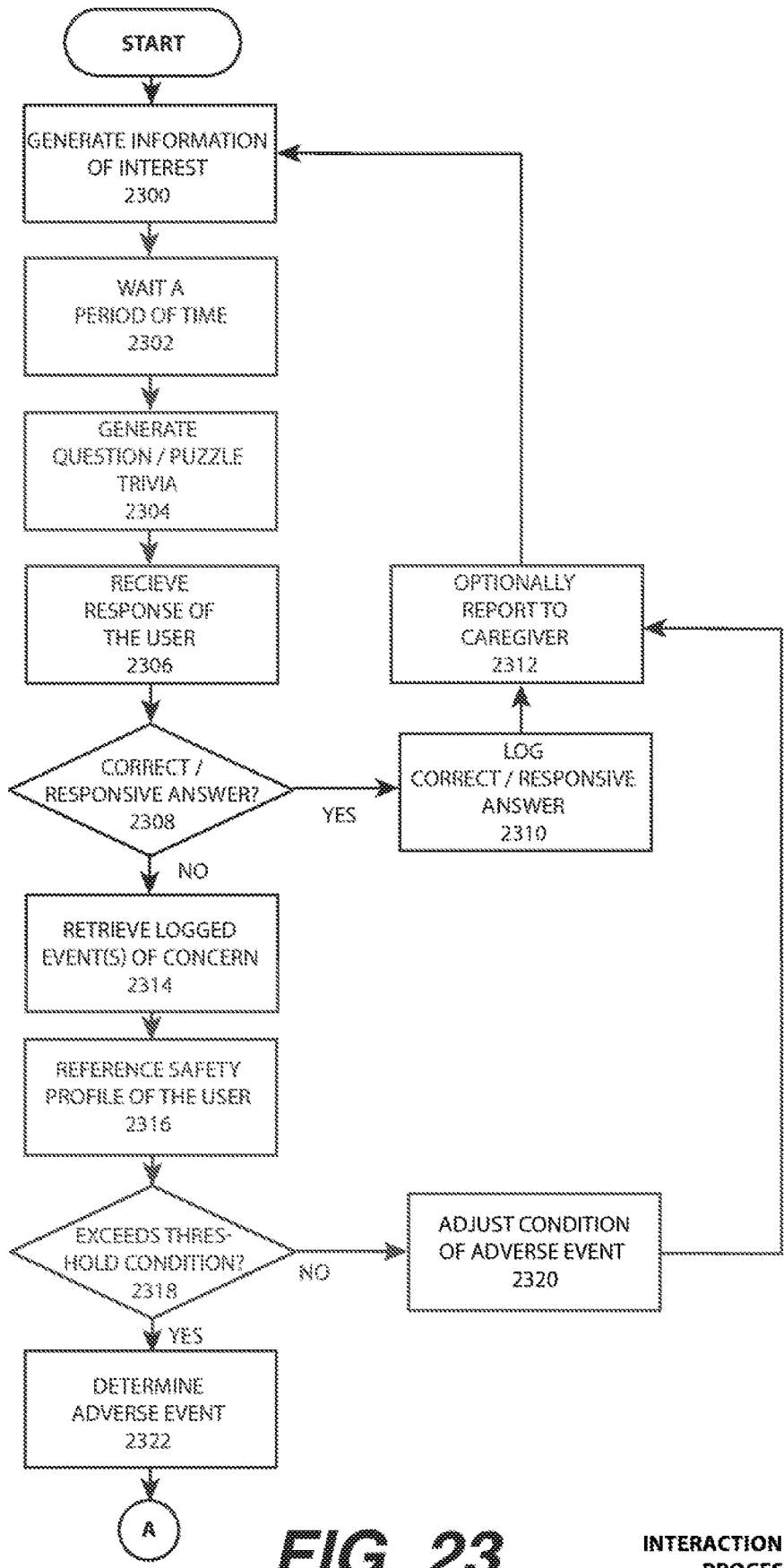
FIG. 23  INTERACTION OF CONCERN PROCESS FLOW

VOICE CONTROLLED ASSISTANCE FOR MONITORING ADVERSE EVENTS OF A USER AND/OR COORDINATING EMERGENCY ACTIONS SUCH AS CAREGIVER COMMUNICATION

CROSS REFERENCE TO RELATED APPLICATIONS

This application is a continuation of U.S. patent application Ser. No. 17/095,224, filed on Nov. 11, 2020 and entitled "VOICE CONTROLLED ASSISTANCE FOR MONITORING ADVERSE EVENTS OF A USER AND/OR COORDINATING EMERGENCY ACTIONS SUCH AS CAREGIVER COMMUNICATION," which is a continuation of U.S. patent application Ser. No. 16/936,019, filed on Jul. 22, 2020 and entitled "VOICE CONTROLLED ASSISTANCE FOR MONITORING ADVERSE EVENTS OF A USER AND/OR COORDINATING EMERGENCY ACTIONS SUCH AS CAREGIVER COMMUNICATION," which is a continuation of U.S. patent application Ser. No. 15/802,705, filed on Nov. 3, 2017 and entitled "VOICE CONTROLLED ASSISTANCE FOR MONITORING ADVERSE EVENTS OF A USER AND/OR COORDINATING EMERGENCY ACTIONS SUCH AS CAREGIVER COMMUNICATION," which is a continuation of U.S. patent application Ser. No. 15/590,012, filed on May 9, 2017 and entitled "VOICE CONTROLLED ASSISTANCE FOR MONITORING ADVERSE EVENTS OF A USER AND/OR COORDINATING EMERGENCY ACTIONS SUCH AS CAREGIVER COMMUNICATION," the contents each being incorporated herein by reference.

FIELD OF TECHNOLOGY

This disclosure relates generally to data processing devices and, more particularly, to a method, a device, a system and/or a manufacture of voice controlled assistance for monitoring adverse events of a user and/or coordinating emergency actions such as caregiver communication.

BACKGROUND

A caregiving organization that provides care to a user within a caregiving environment may need to monitor the user for wellbeing, health, and/or for the safety of the user in case of an incident. For example, a user who is impaired may be unable get up if they fall down, or may be unable to escape a house if the house catches on fire. Similarly, the user may suffer from intermittent memory loss that may be correlated with an increase risk of incident. It may be difficult for the caregiving organization (e.g., a hospital, a hospice care, a in-home healthcare organization), a caregiver (e.g., a hospice worker, a nurse, a family member) providing care to determine how the user is doing and/or a current risk level of the user, including but not limited to in a home care environment. If the user is subject to an incident or begins to undergo a temporary or permanent mental change, the user may have difficulty getting to a communication device (e.g., a phone, a mobile device, a computer, a panic button on a necklace that dials 9-1-1) to contact the caregiver or an emergency service. The caregiver and/or the caregiving organization may therefore have little insight in the user's daily state. As a result, the user may be at increased risk of injury or even death.

At the same time, a voice controlled automated assistance service such as Google Assistant, Amazon Alexa, and Apple Ski may provide a general assistance that may be useful to any user, but may be especially helpful for persons who are impaired, elderly, under treatment in a medical facility, or undergoing home care. For example, the user may more easily interface with technology by using their voice which may be a natural way of communicating for the user. Such services may continue to become increasingly human-like in their responses and interactions. The user may therefore be comforted by voice communications or find companionship with the automated voice assistance service. For example, the user may be able to search the web, order a product from an online retailer, and control household connected devices such as a smart bulb or a connected television. They may therefore by encouraged to interact frequently, provided candid or honest information, and engage with and confide in the automated assistance service.

However, utilizing voice controlled automated assistances services may present some difficulties for a user. Assistance applications of the automated assistance service may have a complicated set of voice inputs or commands that the user may have difficulty remembering or pronouncing. The automated assistance service may have a limited means of customization, including but not limited to voice commands that may invoke assistance applications and initiate assistance actions such as ordering delivery services. Some of these difficulties may be amplified in impaired persons, medical patients and/or the elderly. In addition, the user (and/or the caregiver) may misunderstand a capability of the automated assistance service as it relates to safety of the user. For example, the automated assistance service may be unable to distinguish when a user is in peril versus trying to utilize a general service. The automated assistance service may have no programming to support an emergency response to the incident or call for help by the user.

As a result of these challenges, the caregiving organization and/or the caregiver may not know the user is at increased risk for an incident or that the user is in immediate danger. The user may continue to be subject to a high risk of injury, immediate risk of injury, and/or even risk of death, including as a result of misunderstanding the capabilities of the voice controlled automated assistance service. Other devices meant to aid the user if an incident occurs may be unavailable, require physical possession, and/or be unusable during an emergency due to the user's infrequent use of such devices.

SUMMARY

Disclosed are a method, a device, a system, and/or a manufacture of voice controlled assistance for monitoring adverse events of a user and/or coordinating emergency actions such as caregiver communication.

In one embodiment, an apparatus includes a speaker for generating a verbal status query to a user and a microphone to gather from an immediate environment of the microphone a voice communication of a user and/or an ambient sound of the immediate environment. The apparatus further includes a network interface controller providing communicative coupling to at least one instance of a voice controlled assistance service and at least one instance of an automated emergency assistance service. The apparatus includes a processor and a memory. The memory includes computer-executable instructions that when executed on the processor cause the processor to: (i) generate the verbal status query for the user; (ii) determine occurrence of an event of concern including a non-response event defined as a failure to receive by the microphone a recognizable response from the user; (iii) determine that the event of concern is an adverse event requiring transmission of a notification to a device of a caregiver of the user, and (iv) initiate an alert message notification to the device of the caregiver of the user based on the adverse event.

The apparatus may further include a presence sensor, and the memory may further include computer-executable instructions that when executed on the processor cause the processor to generate the voice status query for the user in response to a sensing event of the presence sensor sensing a presence of the user. The apparatus may include a database to store a safety profile that may specify a condition under which one or more events of concern define the adverse event requiring notification to the device of the caregiver of the user. The memory may further include an assistance service coordinator that includes computer-executable instructions that when executed on the processor cause the processor to, upon determination of the adverse event, automatically re-route a destination of a set of voice communications of the user from a first voice controlled assistance service (that provides a general assistance) to a second voice controlled assistance service providing an automated emergency assistance service to the user.

The apparatus may further include within the memory computer-executable instructions that when executed on the processor cause the processor to repeat the verbal status query to the user and increase a volume of the verbal status query from the speaker following determination of the non-response event of the user. The computer-executable instructions may also, upon occurrence of the event of concern, transmit a status query to a device of the user and/or generate a verbal warning to the user with the speaker. The verbal warning may state that (i) the user has failed to provide the recognizable response, (ii) the caregiver has been alerted, and/or (iii) the emergency service has been alerted. The computer executable instructions may also generate the voice query with the speaker upon detection of a sound spike and/or a vibration spike (e.g., that may indicate that the user has fallen or collided with an object).

The apparatus may further include a particulate sensor to detect within the environment of the user a particulate associated with a first health risk to the user. Similarly, the apparatus may include a chemical sensor to detect within the environment of the user a chemical associated with a second health risk to the user. The memory may include computer-executable instructions that when executed on the processor cause the processor to detect the particulate at the particulate sensor and/or the chemical at the chemical sensor, and determine an adverse event requiring execution of an emergency action based on the detection of the particulate at the particulate sensor and/or the chemical at the chemical sensor. The chemical sensor may be a carbon dioxide sensor and/or a carbon monoxide sensor, and the particulate sensor may be a smoke detector.

The apparatus may further include a user interface, to display a textual message converted from a speech response of the voice controlled assistance server. The memory may further include a speech-text converter including computer-executable instructions that when executed on the processor cause the processor to convert the speech response of the assistance service to the textual message for display on a graphical user interface. The apparatus may also include a video camera, the memory further including computer-executable instructions that when executed on the processor cause the processor to, upon occurrence of the adverse event, establish a video feed between the assistance device and the emergency service and/or the device of the caregiver. The computer readable instructions may also populate the graphical user interface with the textual message converted with the speech-text converter for presentation to the user. The computer executable instructions may determine a threshold inactivity of the device of the user, and the presence sensor may be a motion sensor, an infrared sensor, a proximity sensor, an RFID sensor, a noise sensor, a Bluetooth sensor, and/or a ultrasonic frequency sound sensor.

The event of concern may further include a negative response event of the user defined as a negative response from the user to the verbal status query. The threshold inactivity may be determined based on a GPS coordinate of the device, a network traffic of the device of the user, an accelerometer data of the device of the user, a microphone of the device of the user, and/or a video feed of the device of the user.

The memory may include an assistance service scheduler that includes computer-executable instructions that when executed on the processor cause the processor to define a custom command word and associate the custom command word with an assistance application of a voice controlled assistance service along with an assistance action of the assistance application. The assistance action may conform to a voice command protocol of the assistance application. The memory may pre-specify one or more voice inputs required upon initiation of the assistance action to execute the assistance action of the assistance application, the one or more voice inputs conforming to the voice command protocol of the assistance application. The computer executable instructions may also specify: (i) a confirmation requirement for a verbal confirmation of the user prior to execution of the assistance application and/or (ii) an input request for one or more additional verbal inputs conforming the voice command protocol before execution of the assistance application. The computer executable instructions stored in the memory may schedule execution of the assistance action of the assistance application. The event of concern may further include failure to receive the verbal confirmation of the user and/or a failure to receive the input request for one or more additional verbal inputs.

In another embodiment, a system includes an assistance device communicatively coupled to a voice controlled assistance service over a network. The assistance device includes a speaker of the assistance device, a microphone of the assistance device, a processor of the assistance device, a presence sensor of the assistance device (to sense a presence of a user of the assistance device within an immediate environment of the assistance device), and a memory of the assistance device. The memory includes computer-executable instructions that when executed on the processor cause the processor to, upon sensing the presence of the user, generate a verbal status query to the user including an authorization request for execution of an assistance action of an assistance application of a voice controlled assistance service. The assistance action conforms to a voice command protocol of the assistance application. The computer executable instructions further invoke the assistance application and initiate the assistance action upon receiving an authorization from the user.

The system further includes a sensing pod to expand communication between the user and the assistance device to an extended environment, the sensing pod including a microphone of the sensing pod to gather a sound signal from an immediate environment of the sensing pod that may be determined by the assistance device to be a non-response event of the user to the verbal status query and/or a negative response event of the user defined as a negative response from the user to the verbal status query. The sensing pod further includes a speaker of the sensing pod (optionally to generate the verbal status query), a processor of the sensing pod, a memory of the sensing pod and a wireless transmitter-receiver for communicative coupling with the assistance device over the network to transmit the sound signal. The system may further include a mobile device, a wearable device, including, an automated assistance server (e.g., for providing a general voice assistance of the voice controlled assistance service), an assistance scheduling server (e.g., for streamlining interactions with the automated assistance service and its assistance applications), and an emergency server (e.g., for providing a specialized emergency assistance), and additional elements of each.

In yet another embodiment, a method includes generating with a speaker a verbal status query to a user at a predetermined time, at a random time, upon a sensing event in which a presence of the user is sensed, and/or upon a threshold inactivity of a device of the user. A countdown timer set to a time length is initiated. The method determines occurrence of an event of concern that is (i) a negative response event that is a negative response from the user to the verbal status query, the negative response received by a microphone, and/or (ii) a non-response event that is a failure to receive by the microphone a recognizable response from the user before expiration of the countdown timer, The method references a safety profile specifying a condition under which one or more events of concern define an adverse event requiring execution of an emergency action. The method exterminates occurrence of the adverse event based on the condition of the safety profile and occurrence of the event of concern. The method determines the emergency action requires a notification to a device of a caregiver of the user and/or a device of an emergency service. An alert message is generated for a device of the emergency service and/or the device of the caregiver of the user, the alert message including a log including the adverse event and/or the one or more events of concern.

BRIEF DESCRIPTION OF THE DRAWINGS

The embodiments of this disclosure are illustrated by way of example and not limitation in the figures of the accompanying drawings, in which like references indicate similar elements and in which:

FIG. 18 is an assistance application automation process flow illustrating selection of an assistance application and an assistance action of the assistance application conforming to a voice command protocol, pre-storing one or more voice inputs required upon initiation of the assistance application for its execution, determining any confirmation requirements and/or voice inputs required from the user just prior to execution, and setting a condition for triggering the assistance application, according to one or more embodiments.

FIG. 19 is a customizable command process flow illustrating the automation of the assistance action of FIG. 18 utilizing a custom command word of the user for the user to initiate the assistance application on demand, according to one or more embodiments.

FIG. 20 is an adverse event calibration process flow illustrating adjustment of the determination of the adverse event requiring an emergency action in response to the determination of an event of concern and/or an adverse event, for example by lowing a threshold for determining an event of concern by decreasing a time length of a countdown timer in which the user can respond to the status query before determination of a non-response event, according to one or more embodiments.

FIG. 21 is a personal vitals and environmental hazard emergency action process flow illustrating detection by the assistance device of FIG. 2 and/or the sensing pod of FIG. 3 an adverse vital sign of the user and/or an environmental hazard, the sensing of the personal vital sign and/or the environmental hazard (e.g., smoke or carbon monoxide) determined to be an adverse event triggering a warning to the user within the caregiving environment, an alert message to the caregiver, an alert message to the emergency service, and/or additional emergency actions, according to one or more embodiments.

FIG. 22 is a user message process flow illustrating a process by which the user may store an away message associated with an expected inactivity time suspending a generation of one or more verbal status queries to the user, the away message communicated to the caregiver automatically and/or upon the non-response event, according to one or more embodiments.

FIG. 23 is an interaction of concern process flow illustrating a status query that may be in the form of a question, a puzzle, a quiz, or a trivia to determine a cognitive ability of the user including determination of an event of concern for incorrect and/or non-responsive answers, according to one or more embodiments.

Other features of the present embodiments will be apparent from the accompanying drawings and from the detailed description that follows.

DETAILED DESCRIPTION

Disclosed are a method, a device, a system and/or a manufacture of voice controlled assistance for monitoring adverse events of a user and/or coordinating emergency actions such as caregiver communication. Although the present embodiments have been described with reference to specific example embodiments, it will be evident that various modifications and changes may be made to these embodiments without departing from the broader spirit and scope of the various embodiments.

Figure 1:
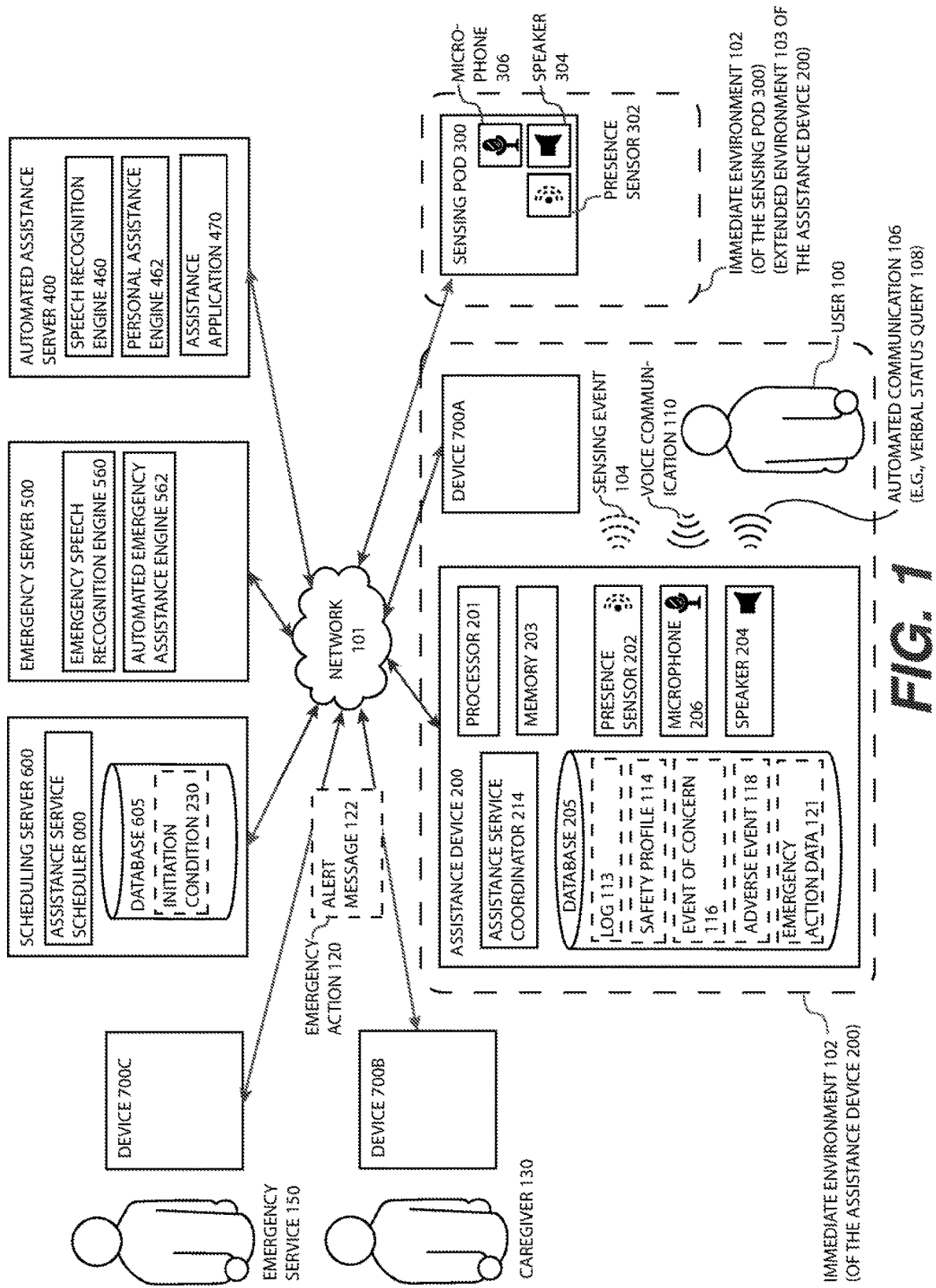
FIG. 1 illustrates an assistance coordination network comprising an assistance device, a sensing pod, an automated assistance server to provide a general assistance to a user, an emergency server to provide an emergency assistance to the user, a scheduling server, and one or more devices, with one aspect of the assistance coordination network further illustrated in which the assistance device generates an automated communication (for example, a verbal status query such as "Good morning, how are you?") to which the user responds with a voice communication which may be determined to be an event of concern (for example, the voice response of "I feel sick") that may additionally be determined to be an adverse event (e.g., exceeding three instances of a negative response event), the adverse event triggering an emergency action such as notifying a caregiver of the user, notifying an emergency service, and/or re-routing the voice communications of the user from the automated assistance server to the emergency server, according to one or more embodiments.

FIG. 1 illustrates an assistance coordination network comprising an assistance device 200, a sensing pod 300, an automated assistance server 400 to provide a general assistance to a user 100, an emergency server 500 to provide an emergency assistance to the user 100, a scheduling server 600, and one or more devices 700A through 700C for communication between and among the user 100, a caregiver 130, and/or an emergency service 150, according to one or more embodiments. In the embodiment of FIG. 1, one aspect of the assistance coordination network is illustrated in which a user 100 within a caregiving environment (e.g., a house where the user 100 is receiving homecare, a nursing facility, a hospital) is further within an immediate environment 102A of the assistance device 200. The immediate environment 102 of the assistance device 200 is an area around the assistance device 200 in which the assistance device 200 can reliably receive on a microphone and recognize verbal communications of a user 100 under a normal range of speech decibels (e.g., approximately 60 decibels to 90 decibels at a point of origin). For example, the immediate environment 102 may be a large living room, a radius of 40 feet around the assistance device 200, two adjacent rooms within a home, a back yard, etc. The immediate environment 102 may depend on a microphone sensitivity and/or a voice recognition capability of the assistance device 200 and/or voice recognition capability of services accessible through the assistance device 200.

In the embodiment of FIG. 1 the user 100 may interact through the assistance device 200 and the sensing pod 300 with an automated assistance service operating from an automated assistance server 400. The automated assistance service is a voice controlled automated assistance service that is software and/or computer code that provides a general assistance, for example, Apple Ski, Google Assistant, Samsung Bixby, and/or Amazon Alexa. The user 100 may be able to use a voice command to search the web, find out the weather, order a product from an e-commerce retail store, control a connected device such as a household thermostat, light, or speaker, and/or engage in similar actions. Speech responses (e.g., an automated communication 106) are generated by a personal assistance engine 462 of the automated assistance server 400 that may be proprietary and/or open source software that implements "artificial intelligence" interactions and synthetic personalities. The automated assistance service 400 may include one or more assistance applications 470 that are voice controlled software applications accessible through the automated assistance service (e.g., "Alexa Skills") and that may provide the user 100 with a specialized service, for example ordering a specific product from a specific vendor (e.g., an application or ordering a pizza from a certain pizza company).

While the user 100 in the caregiving environment may engage in general communication and voice interactions with the automated assistance server 400, the assistance device 200 may act as an additional interface and/or voice controlled interface to the automated assistance service implemented via the automated assistance server 400. As the additional interface to the automated assistance server 400, the assistance device 200 may provide streamlined commands that may help the user 100 to utilize the assistance applications and assistance actions of the assistance applications (e.g., the assistance application 470 of and the assistance actions 478 of FIG. 4). However, the assistance device 200 acting as the additional interface may also provide an integrated monitoring capability that monitors and/or analyzes the user 100 including in the user 100's interactions or attempted interactions with the automated assistance service, according to one or more embodiments. This may provide frequent and/or accurate data due to the user 100's familiar with user, high level of utility, and engaging social interaction.

In the embodiment of FIG. 1, the monitoring may begin upon a sensing event 104 by the assistance device 200. The sensing event 104 may occur by determining a sound of the user 100 in the immediate environment 102A of the assistance device 200 or upon sensing the user 100 and/or a device of the user 100 with a presence sensor 202 utilizing other means than sound. The assistance device 200 may then trigger an automated communication 106 from the speaker 204. Specifically, in the embodiment of FIG. 1, the automated communication 106 is a verbal status query 108 to the user 100. The verbal status query 108 may be a verbal question or interrogatory generated as an audio signal and usable to elicit a response from the user, the response usable to determine a state, a disposition, a feeling, an emotion, a condition (e.g., physical, mental, psychological, and/or emotional) and/or a status of the user 100. The user 100 may reply to the verbal status query 108 with a voice communication 110 which is received by a microphone 206 of the assistance device 200. The response of the user 100 may be analyzed and determined to be a negative response event (e.g., the negative response event 115, not shown in FIG. 1) or a positive response event (e.g., the positive response event 119, also not shown in FIG. 1), the determination made either locally at the assistance device 200, at the emergency server 500, and/or at another location. The negative response event 115, the positive response event 119, or a non-response event 117 (as shown and described in conjunction with FIG. 10) are data that may be logged in a database 205 of the assistance device 200. The positive response event 119 may be logged in a log 113 (as shown and described in conjunction with FIG. 2). The log 113 may be periodically provided to the device 700B of the caregiver 130 in the form of a report, even if log primarily (or exclusively) comprises instances of the positive response event 119. In contrast, the negative response event 115 and the non-response event 117 are each instances of an event of concern 116. Occurrence of one or more of the events of concern 116, under such conditions as may be specified in a safety profile 114 of the user 100, may equate to an adverse event 118 requiring an emergency action 120 such as a notification of a caregiver 130 of the user 100.

For example, in the embodiment of FIG. 1 the presence of the user 100 within the immediate environment 102A of the assistance device 200 may be sensed through the sound of the user 100's footsteps above an ambient sound threshold of the immediate environment 102A. The assistance device 200 may generate a verbal status query 108 such as "How are you doing today?". In reply, the user 100 may generate a voice communication 110 that is a voice response such as "I'm doing ok." The assistance device 200 may generate a second statue query 108 such as "How is your knee feeling?" based on information previously stored about the user 100 in the safety profile 114. The user 100 may reply "It hurts." The first voice response of the user 100 may be determined to be a positive response event 119 and the second voice response of the user 100 may be determined to be the negative response event 115 that may arise to an event of concern 116.

The assistance device 200 may then reference the log 113 and the safety profile 114. The safety profile 114 comprises data specifying a condition under which one or more events of concern 116 define an adverse event 118 that requires execution of an emergency action 120. In the embodiment of FIG. 1, for example, the safety profile 114 of the user 100 may specify that an adverse event 118 occurs any time the user 100 generates: (i) more than three instances of the negative response event 117 within a twenty-four hour period; (ii) more than five instances of any event of concern 116 (including instances of the non-response event 117); or (iii) any negative response event 117 related to the user 100's knee or current prescribed medication. In addition to a local determination of the event of concern 116, a signal of the voice communication 110 may be communicated through a network 101 to the automated assistance server 400 and/or the emergency server 500 for the determination.

Upon determination of the adverse event 118, the assistance device 200 may determine one or more instances of the emergency action data 121 that apply (e.g., by referencing the safety profile 114) and execute an emergency action 120 associated with the emergency action data 121. In the embodiment of FIG. 1 the emergency action data 121 specifies an alert message 122 to be generated along with the data required for routing the message. In the embodiment of FIG. 1 the emergency action 120 is the specific communication of the alert message 122. The alert message 122 includes the log 113 comprising one or more instances of the negative response event 115 forming the basis of the alert message 122. For example, the log 113 may include the negative response event 115 that is a text string of the response of the user 100 to the verbal status query 108: "Did you take your medicine this morning?" The user 100 may have replied "No, I didn't feel well."

The alert message 122 is communicated through the network 101 to the device 700B of the caregiver 130 and/or the device 700C of the emergency service 150. The network 101 may be the internet, a local area network, a wide area network, a mesh network implemented by communication device-to-device, and/or a virtual private network. The device 700B and/or the Device 700C may be a mobile device (e.g., a smartphone, a cell phone), a wearable device, a desktop computer, and/or a tablet device. The device 700C may also be a server of the emergency service 150 that may route, respond to, and/or allocate emergency resources to emergency calls and/or other emergency-related electronic communications. The emergency service, for example, may be a police department, a fire department, a hospital, a poison control center, and/or similar agencies and enterprises. In one or more embodiments, where the adverse event 118 may be of lesser concern (e.g., two consecutive instances of the negative response event 115) the alert message 122 may be transmitted exclusively to the device 700B of the caregiver 130. In one or more other embodiments, the alert message 122 may be of greater concern (e.g., five consecutive instances of the non-response event 117), and the alert message may be sent to the device 700C of the emergency service 150 and/or the device 700B of the caregiver 130. The result will be to inform the caregiver 130 and/or the emergency 150 that the user 100 may be having difficulty or even may be in imminent peril.

Upon receipt of the alert message 122 the caregiver 130 may be able to take actions on the device 700B such as initiate an audio feed (e.g., the audio feed 350 of FIG. 3) or a video feed (e.g., the video feed 352 of FIG. 3) from the assistance device 200 and/or the sensing device 300, and/or initiate a two-way audio and/or visual communication channel between the device 700B and the assistance device 200 and/or the sensing pod 300. The device 700C may have a similar capability.

In addition to generating the alert message 122, additional instances of the emergency action 120 include but are not limited to automatically establishing the audio feed 350 and/or the video feed 352, changing parameters of the safety profile 114 such as under what conditions a response of the user 100 will be determined to be an event of concern 116 and/or under what conditions the event of concern 116 will be determined to be the adverse event 118, and altering which server primarily receives and parses the voice communications of the user 100 (e.g., the automated assistance server 400 or the emergency server 500). For example, one type of emergency action 120 specified in the emergency action data 121 may be to re-route the voice communication 110 of the user 100 to the emergency server 500 such that an emergency speech recognition engine 560 is primarily utilized to determine speech and/or speech patterns of the user 100 (e.g., a stressed tone of voice, lower tolerance for determination that a word sound signal should be recognized as "help", recognition of profanity or expletives, etc.).

In another example, the emergency action 120 may adjust what future instances of the emergency action 120 should be taken upon occurrence of the adverse event 118 (e.g., by altering the instructions or data in the emergency action data 121 and/or the safety profile 114). For example, a first instance of an adverse event 118 may initiate the emergency action 120 of sending the alert message 122 to a first caregiver 130A (not shown in the embodiment of FIG. 1). The emergency action 120 in this case may also update the safety profile 114 such that the next instance of the adverse event 118 may expand a scope of a next instance of the alert message 122. For example, when the emergency action 120 is triggered again, both the first caregiver 130A and a second caregiver 130B may receive the alert message 122.

Figure 4:
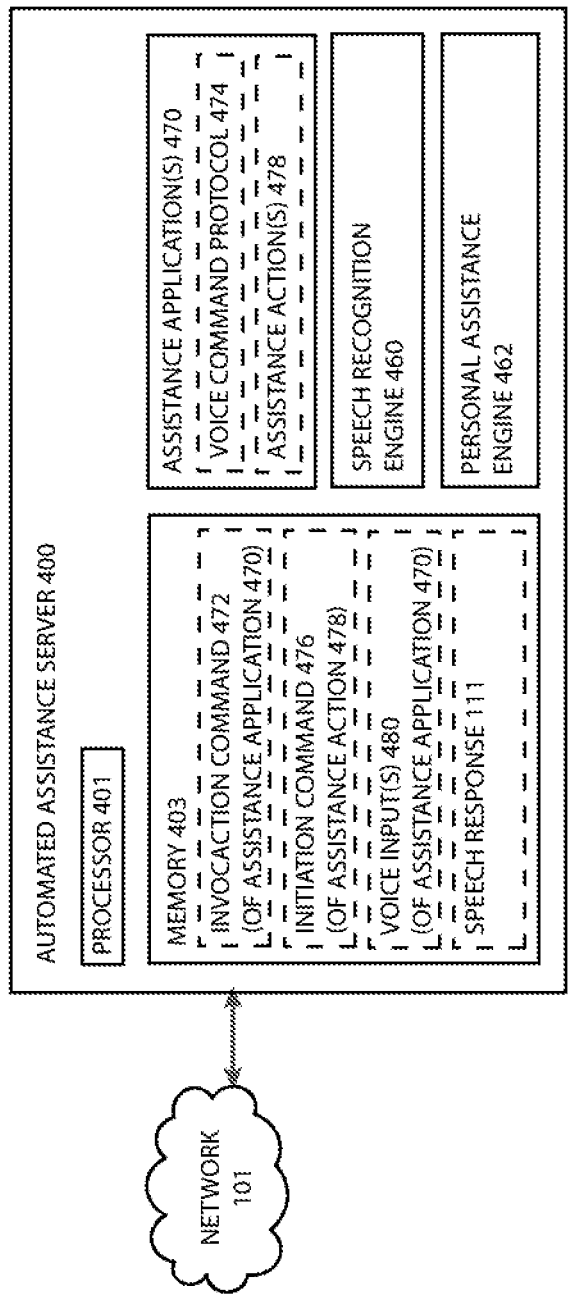
FIG. 4 illustrates the automated assistance server of FIG. 1 for providing a general assistance to the user (for example, initiating a web search, ordering a product, engaging in a social interaction, and similar functions), the automated assistance server including a speech recognition engine to recognize and/or translate a speech of the user, a personal assistance engine for providing the general assistance and generating speech responses for the user, and one or more assistance applications that can be invoked by an invocation command and that carry out an assistance action initiated by an initiation command, according to one or more embodiments.
Figure 6:
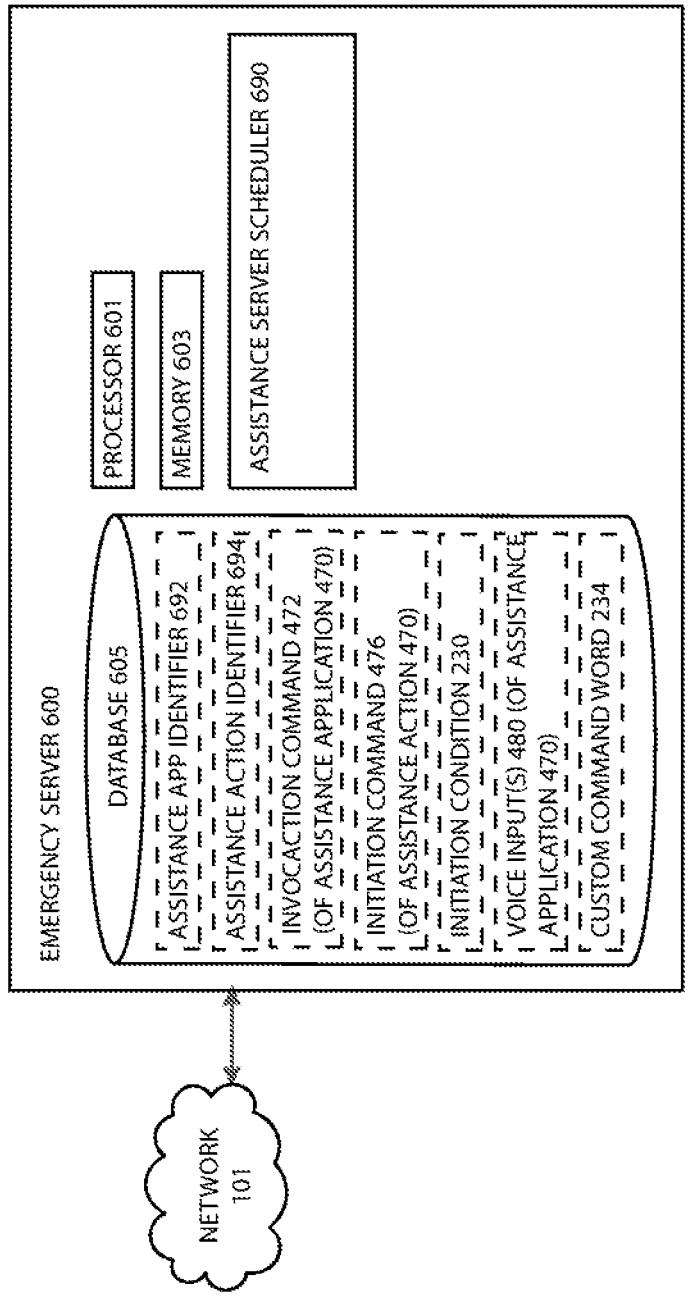
FIG. 6 illustrates the scheduling server of FIG. 1 including an assistance service scheduler that may associate and store the invocation command, the initiation command, and a set of one or more voice inputs of FIG. 4 that may be required for execution of the assistance application, the scheduling server capable of initiating the assistance action upon occurrence of an initiation condition to aid in providing the general assistance to the user and/or for coordination with the emergency server in determining the event of concern in relation to the user's interaction during the general assistance, according to one or more embodiments.

In one or more embodiments, the scheduling server 600 schedules and initiates assistance actions 478 of assistance applications 478, as shown and described in conjunction with FIG. 4 and FIG. 6, and the process flows of FIG. 18 and FIG. 19. The scheduled instances of the assistance action 478 may allow for streamlined interaction from a perspective of the user 100, especially where the user 100 is physically impaired, may have difficulties articulating words, and/or may have difficulties with their memory. However, the scheduling server 600 may also provide a synergistic opportunity for interacting with the user 100 such that the state of the user 100 can be determined. For example, where the assistance device 200 and/or the emergency server 500 are programmed to evaluate appropriate responses of the user 100, a voice input to the assistance application 470 (e.g., the voice input 480 of FIG. 4) may be used to determine the negative response event 115. For example, where an assistance application 470 for the delivery of food may ask for an address, the assistance device 200 may request the street address from the user 100. If the user 100 responds with an address not matching the street address associated with the user 100 or a street address where the user 100's device 700A is not currently located, then the response of the user 100 may be determined to be a negative response event 117. In this case (e.g., where such analysis has been defined in the instructions of the assistance device 200 and/or the emergency server 500), a request for the voice input 480 by the assistance device 200 acts as the verbal status query 108 to the user 100.

Although not shown in the embodiment of FIG. 1, there may be multiple instances of the user 100 which may be individually authenticated by a voice pattern, a device 700A, or other means of identification to ensure the user 100 is matched to their corresponding instance of the safety profile 114. For example, the caregiving environment may have multiple residents, or an elderly couple may live inside a home together. However, in one or more embodiments there may be a standard version of the safety profile 114 that applies to two or more of the users 100 within a multi-user caregiving environment. The caregiver 130 may also reside in the caregiving environment or generally remain on-site (e.g., at a nursing home). Similarly, there may be coordinated within the caregiving environment multiple instances of the assistance device 200 and/or the sensing pod 300 to provide an extended environment (e.g., the extended environment 103) through which the one or more users 100 may communicate with aspects of the assistance coordination network of FIG. 1. In one or more embodiments the assistance device 200 and each instance of the sensing pod 300 may form a wireless mesh network where, for example, WiFi from one or more wireless routers may have trouble covering some areas of the caregiving environment. In addition there may be multiple instances of the caregiver 130 or the emergency service 150, each with one or more instances of the device 700. In one or more embodiments there may additionally be multiple instances of the automated assistance server 400, either accessible through a common provider of voice controlled assistance (e.g., Amazon Alexa) or through multiple providers of voice controlled assistance (e.g., Amazon Alexa and Apple Ski).

Figure 2:
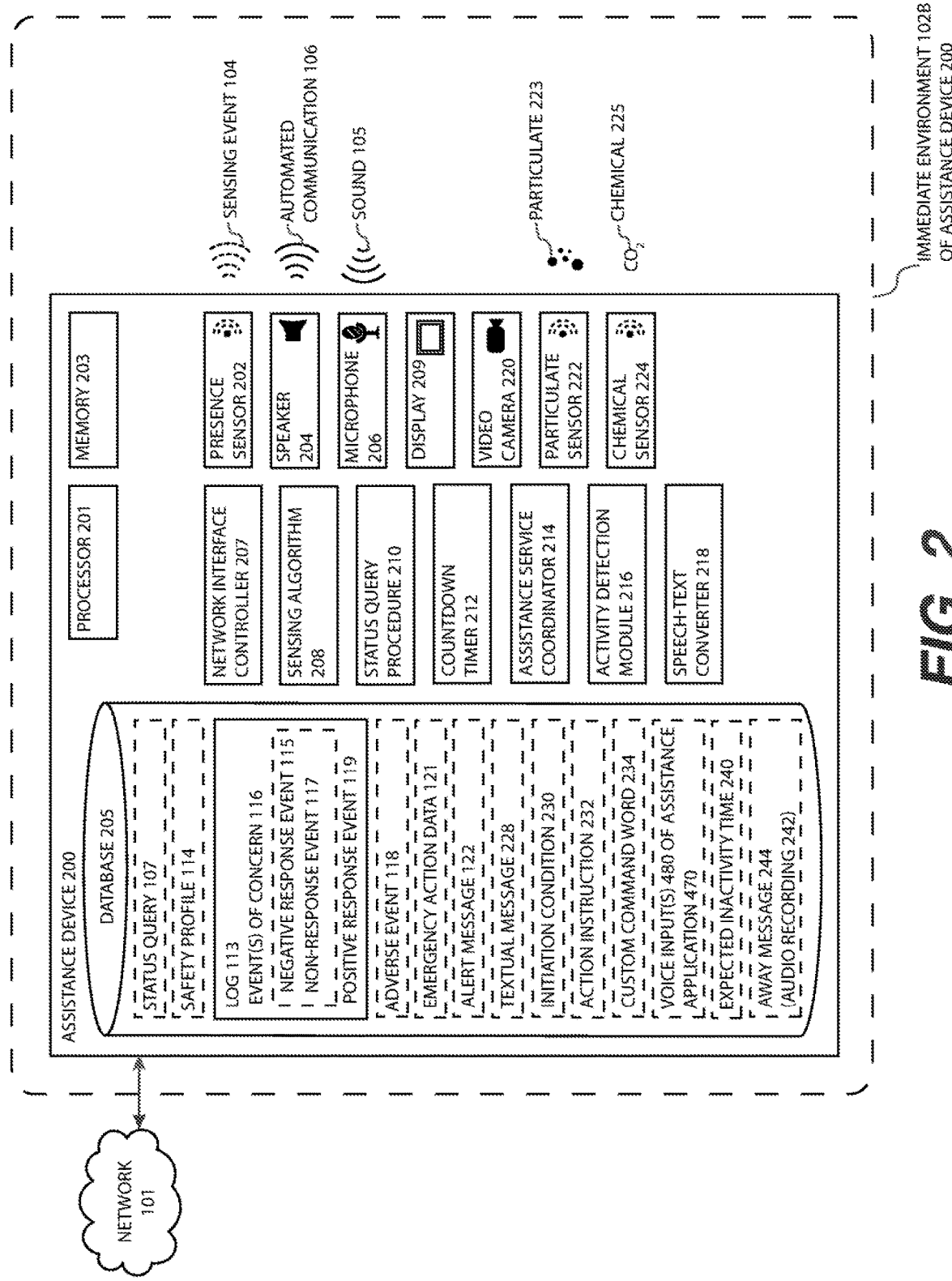
FIG. 2 illustrates the assistance device of FIG. 1, including a presence sensor that may determine a presence of the user in a sensing event to initiate the verbal status query, a sensing algorithm, a countdown timer, a status query procedure, an assistance service coordinator, and a database comprising a custom command word, an action instruction to streamline usage of an assistance application of the automated assistance service, and a log of responses of the user including but not limited to a negative response event, a non-response event, and a positive response event, according to one or more embodiments.

FIG. 2 illustrates the assistance device 200 according to one or more embodiments. Each component shown within the sound assistance device 200 is connected to each other component of the assistance device 200, for example through a data bus, wiring, or other data communication systems and methods. The assistance device 200 is communicatively coupled to the network 101 is surrounded by an immediate environment 102. For example the immediate environment may be a single room, a radius of 20 feet from the assistance device 200, or a radius of 70 feet from the assistance device 200. The assistance device 200 includes a processor 201 that is a computer processor and a memory 203 that is a physical computer memory, each of which are communicatively coupled to each of the components of FIG. 2. The assistance device 200 may include a presence sensor 202 that may be specifically used to sense a presence of the user 100 to generate data usable to determine the sensing event 104. For example, the presence sensor 202 may be a motion sensor, an infrared sensor, an RFID sensor that senses proximity of a radio frequency identification chip, a noise sensor, a light sensor, a vibration sensor, a Bluetooth sensor that senses proximity of the device 700 of the user 100 through a Bluetooth connection, and/or an ultrasonic frequency sound sensor that detects an ultrasonic sound frequency emitted from the device 700 of the user 100. The assistance device 200 includes a speaker 204 that can generate the automated communication 106 and a microphone 206 that can receive a sound 105 from the immediate environment 102. For example, the sound 105 may include an ambient sound, a voice response of the user 100, and/or additional noises. In one or more embodiments the microphone 206 may be used as the presence sensor 202 when the sensing algorithm 208 is configured to analyze sound of the immediate environment 102 to determine the presence of the user 100. The assistance device 200 also includes a network interface controller 210 for communication over the network 101. The network interface controller 210 may implement the electronic circuitry required to communicate using a specific physical layer and data link layer standard such as Ethernet, Fibre Channel, Wi-Fi or Token Ring and may allow for the connection of the assistance device 200 to each of the other devices and servers through the network 101 within the assistance coordination network of FIG. 1. The assistance device 200 may include a display 109 that may display text and/or graphics to the user 100, including a graphical user interface. For example, the display 109 may be a liquid crystal display (LCD) screen.

The sensing algorithm 208 is a set of computer executable instructions usable by the processor 201 to determine with a high probability a presence of the user 100 based upon data inputs from the presence sensor 202. For example, the sensing algorithm 208 may determine a presence of the user 100 when a signal strength of an electromagnetic signal reaches a threshold strength, when "pings" of the device 700 of the user 100 within a timeframe reach a threshold number, and/or when the sound 105 of the immediate environment 102 raises above a threshold level that may be calculated statically (e.g., set to a decibel level) or re-factored continuously (e.g., adjusted based on the ambient sound of the immediate environment 102). Upon the sensing event 104 that may have a high degree of certainty in determining a presence of the user 100 within the immediate environment 102 the sensing algorithm 208 may generate data to be acted on by a status query procedure 210 or initiate additional actions such as to log the sensing event 104 and/or add the sensing event 104 to the log 113.

Determination of the sensing event 104 may initiate a procedure call or otherwise transmit data to the status query procedure 210. The status query procedure 210 is a set of computer executable instructions usable by the processor 201 to determine whether to initiate the status query 107. The status query 107 may be a question or interrogatory generated as data and usable to elicit a response to determine a state, a disposition, a feeling, an emotion, a condition (e.g., physical, mental, psychological, and/or emotional) and/or a status of the user 100. For example, the status query 107 may be a text message sent to a device 700 of the user 100. In one or more embodiments, the status query 107 is the verbal status query 108 generated by the speaker 204 of the assistance device 200.

The status query procedure 210 may determine under what circumstances and what kinds of the status query 107 to generate. For example, where the sensing event 104 is determined through detection of the sound 105, the status query procedure 210 may generate the verbal status query 108, whereas if the sensing event 104 is determined through a GPS coordinate of a device 700 of the user 100 (e.g., the GPS coordinate of a mobile device 750) the status query 107 may be the text message sent to the device 700 of the user 100.

The status query procedure 210 may also include computer executable instructions that when executed on the processor 201 determines that the status query 107 should be expanded from the immediate environment 102 of the assistance device 200 (and/or the immediate environment 102 of a sensing pod 300 that generated data to indicate the presence of the user 100) to the extended environment 103 (e.g., all instances of the sensing pod 300 communicatively coupled to the assistance device 200 in the caregiving environment may repeat the verbal status query 108). For example, following a non-response event 117, the status query procedure 210 may repeat the verbal status query 108 within the extended environment 103 and additionally generate the status query 107 as a text message send to the mobile device of the user 100.

The countdown timer 212 is a software and/or hardware timer initiated during certain actions of the assistance device 200. For example, upon generating the status query 107 the countdown timer 212 may be set to a time length (e.g., 1 minute, 10 seconds, 1 second, 900 milliseconds) by which the user 100 must begin to provide or completely provide the voice communication 110 that is a verbal response. In one example, the countdown timer 212 of four seconds is initiated upon generation of the verbal status query 108. Failure of the user 100 to generate any sound may then result in a non-response event 117 and/or the extension of the verbal status query 108 to the extended environment 103. In a more complex example, the verbal status query 108 of "What time of day is it?" may initiate a 20 second timer in which the user 100 must give the verbal response before determination of a non-response event 117, but also initiate a 10 second timer the expiration of which results in a negative response event 115 even if the user 100 answers before expiration of 20 seconds (e.g., the user 100 was responsive but was unable to tell the time quickly, possibly indicating cognitive confusion). Additionally in this example, failure to answer the correct time by plus or minus fifteen minutes could result in a determination of a negative response event 115. This example may be a form of a quiz, a puzzle, or a trivia as shown and described in conjunction with FIG. 23.

The assistance service coordinator 214 is a set of computer executable instructions that when executed on the processor 201 cause the processor 201 to allocate data communications between the automated assistance server 400 and the emergency server 500. In one or more embodiments: under certain predetermined conditions the assistance service coordinator 214 may transmit all or almost all instances of the voice communication 110 of the user 100 to the automated assistance server 400 to provide the general assistance; whereas under other predetermined conditions the assistance service coordinator 214 may route all or substantially all of the voice communication 110 to the emergency server 500.

In one or more embodiments, upon the adverse event 118 based on one or more instances of the non-response event 117, the assistance service coordinator 214 may terminate communications with the automated assistance server 400 and transmit any subsequently received instance of the voice communication 110 to the emergency server 500 through the network 101. Similarly, the assistance service coordinator 214 may re-route communications upon an event of concern 116 and/or in response to the emergency action 120. Where a two-way communication is established between the device 700B of the caretaker 130 and the assistance device 200 the user 100 the assistance service coordinator 214 may terminate all communication with the automated assistance server 400 such that the interaction between the caregiver 130 and the user 100 is not adversely affected by the automated communication 106. In one or more other embodiments, the assistance service coordinator 214 may also forward a voice communication 110 to both the automated assistance server 400 and the emergency server 500. Where the emergency speech recognition engine 560 determines that the forwarded data includes one or more emergency words, phrases, stressed voice tones, or other indicators of an adverse event 118 requiring execution of the emergency action 120, then the emergency server 500 may communicate a signal to the assistance service coordinator 214 to re-route all voice communication 110 to the emergency server 500. The re-routing may occur by changing an application layer communication protocol for packaging an audio file or audio data stream containing the voice communication 110 of the user 100 and changing a destination address on the network 101 (e.g., an internet protocol (IP) address).

The activity detection module 216 is a set of computer executable instructions that when executed on the processor 201 determine a threshold inactivity level of the user 100 by receiving data from the device 700 of the user 100, the sensing pod 300 and/or another source. In one or more embodiments, the activity detection module 216 receives accelerometer data from the device 700 of the user 100 (e.g., the accelerometer 725 of a mobile device 750) to determine the user 100 is likely moving and therefore is likely in an active state. A threshold inactivity may also be determined based on movement of a GPS coordinate of the device 700 of the user 100, a network traffic of the device 700 of the user 100 (e.g., internet browsing activity on a desktop computer within a 24-hour period), the microphone 706 of the device 700 of the user, and/or graphical analysis or light intensity analysis on a video feed and/or video camera 720 of the device 700 of the user 100.

The speech-text converter 218 is a set of computer executable instructions that when executed on the processor 201 converts data in a text format (e.g., a text string, a text file) into an audio format, and/or may convert the voice communication 110 and/or the automated communication 106 into a text format via a limited speech recognition capability and/or basic sound matching with stored audio files. For example, the speech-text converter may be used to convert a voice communication by the emergency service 150 into a text format for display to the user 100 on the display 209 of the device 200. Conversely, the caregiver 130 may send a text message from the mobile device of the caregiver 130 to the assistance device 200 that converts into a speech communication to the user 100 via the speaker 204.

The assistance device 200 may also include a video camera 200 for recording a video signal for processing, analysis, storage and/or transmission by the assistance device 200. In one or more embodiments the video camera 220 begins to generate a video feed 352 stored and/or communicated to the device 700B of the caregiver 130 and/or the device 700C of the emergency service 150 upon determination of the adverse event 118.

The assistance device 200 may also include a number of other sensors to improve monitoring and safety of the user 100, including detection within the caregiving environment of the user 100 a health risk to the user 100. In the embodiment of FIG. 2, the assistance device 200 includes a particulate sensor 222 and a chemical sensor 224. The particulate sensor 222 may detect a particulate 223 within the immediate environment 102. For example the particulate 223 may include smoke, steam, smog, dust, soot and/or other harmful suspensions in air. In one or more embodiments the particulate sensor 222 is a smoke detector and the particulate 223 is smoke. The chemical sensor 224 may detect a chemical 225 that me be harmful to the user 100 at one or more concentrations. For example, the chemical 225 may be carbon dioxide, carbon monoxide, cyanide gas, ammonia, oxygen (including lack of or over abundance of oxygen), ozone, nitrous oxides, sulfurous oxides, volatile organic compounds, and similar hazardous molecules. Although not shown in the embodiment of FIG. 2, a biological sensor (e.g., to detect a mold, a bacteria, a fungi) may also be employed to detect environmental hazards.

In addition to hardware elements and computer executable instructions the assistance device 200 includes numerous data within a database 205 that may be stored on the memory 203 (e.g., random access memory (RAM), a storage device (e.g., a disk, a solid-state memory), a volatile memory, a memrister, a solid-state memory). The database 205 may store one or more instances of the status query 107, for example a basic phrase that may be read and initiated as the verbal status query 108 ("How are you?") by the status query procedure 210. The status query 107 may also be transmitted through the network 101 from the automated assistance server 400, the emergency server 500 and/or the scheduling server 600 in which case the status query 107 may exist temporarily or instantaneously within the database 205 and/or the memory 203. The status query 107 may be stored as an audio file, or may be stored as a text file that may be converted by the speech-text converter 218 into the verbal status query 108.

The database 205 may further include the safety profile 114 of the user 100. The safety profile 114 comprises conditions under which one or more events of concern 116 constitute an adverse event 118, and may also include the emergency action data 121 to be taken upon determination of a particular type of the adverse event 118 defined and stored as the emergency action data 121. Although shown separate in the embodiment of FIG. 2, the emergency action data 121 may be associated with and/or stored within the safety profile 114. In one or more embodiments, the safety profile 114 may specify a decision tree and/or a complex decision tree for determination of which instances of the emergency action 120 are to be taken in response to an adverse event 118 (e.g., which instances of the emergency action data 121 should be executed under which circumstances). For example, one process by which determination of instances of the emergency action 120 are taken is shown and described in conjunction with FIG. 15. The safety profile 114 may be unique to a particular instance of the user 100 and custom built for the particular user 100's needs and/or concerns. The safety profile 114 may also be selectable and updatable by the caretaker 130 based on several available pre-generated profiles. Additionally, the safety profile 114 may be standard for all or many instances of the user 100 (e.g., a standard factory setting that may have shown a good result or a result with a low number of false events of concern 116). In addition, the safety profile 114 may be continuously updated through updates from the network 101 and/or through machine learning algorithms that may adjust to patterns or activities of an instance of the user 100 (e.g., a non-response event 117 from one particular instance of the sensing pod 300 within the caregiving environment of the user 100 is not considered an event of concern 116 when a high level of ambient noise exists within the immediate environment 102, for example because a television may create too much noise for the user 100 to hear the verbal status query 108).

The log 113 is a list of responses of the user 100 and may include metadata associated with the responses such as a time of the response, a risk score of the response, an assistance device 200 and/or a sensing pod 300 from which the response was received, etc. The log 113 may include responses of the user 100 including various queries translated into text or stored as audio files and/or designations of the negative response event 115, the non-response event 117, and/or the positive response event 119. The log 113 and/or parts of the log 113 may be communicated to the device 700 of the caretaker 130, the device 700 of the emergency service 150, and/or even the device 700 of the user 100. The log 113 may also be backed up or even primarily stored on the emergency server 500. The log 113 may also store the adverse event 118 and associated meta data (or the adverse event 118 may be stored in a separate log).

The database 205 may additionally store an alert message 122 generated as one possible instance of the emergency action 120. The alert message 122 may include the log 113 and/or data of the log 113 such as one or more events of concern 116 giving rise to the determination of the adverse event 118. For example, the alert message 122 may be the message: "Hello. Janet has been non-responsive during two status checks today. The first check-in was at 9:02 AM. The second check-in was at 11:46 AM".

In one or more embodiments, the scheduling server 600 as shown and described in conjunction with FIG. 6 may store in the database 605 an invocation command 472 and an initiation command 476 of an assistance application 470. However, the invocation command 472, the initiation command 476, and/or one or more voice inputs 480 may also be stored in the database 205. Where stored in the database 205, the scheduling server 600 may transmit the action instruction 232 to the assistance device 200 to initiate the invocation command 472, the initiation command 476, and/or any voice inputs 480, as transmitted from the assistance device 200. In other words, a condition triggering the assistance application 470 may occur on the scheduling server 600 as shown and described in conjunction with FIG. 6, but the assistance application 470 may be invoked from the assistance device 200.

The database 205 may include a textual message 228 that may be a text version of the automated communication 106 to be presented to the user 100 on the display 209 of the assistance device 200. For example, the textual message 228 may be generated by the automated assistance server 400 or converted from an audio speech communication of the automated assistance server 400 with the speech-text converter 218. Similarly, the emergency server 500 may transmit the textual message 228 and/or data converted into the textual message 228 for display to the user 100 in a graphical user interface. The textual message 228 can also be forwarded to the device 700 of the user 100.

The embodiment of FIG. 2 further may include one or more pieces of data for automatically invoking and/or streamlining activation of one or more instances of the assistance application 470, including an initiation condition 230 of an assistance action 478, an action instruction 232, a custom command word 234, and one or more voice inputs 236 required before completion of the execution of the assistance action 478. This data is described in conjunction with the assistance server 400 of FIG. 4. Additionally, the assistance device 200 may further include an away message 244 of the user 100 that is stored as an audio recording 242 and an expected inactivity time 240 that is a length of time specified as data associated with the audio recording 242. The expected inactivity time 240 may be usable to suspend instances of the status query 107, usable as notification to the caregiver 130 of an activity of the user 100 away from the caregiving environment, and/or for additional purposes. The away message 244 and the expected inactivity time 240 are shown and described in conjunction with the process flow of FIG. 22.

Figure 3:
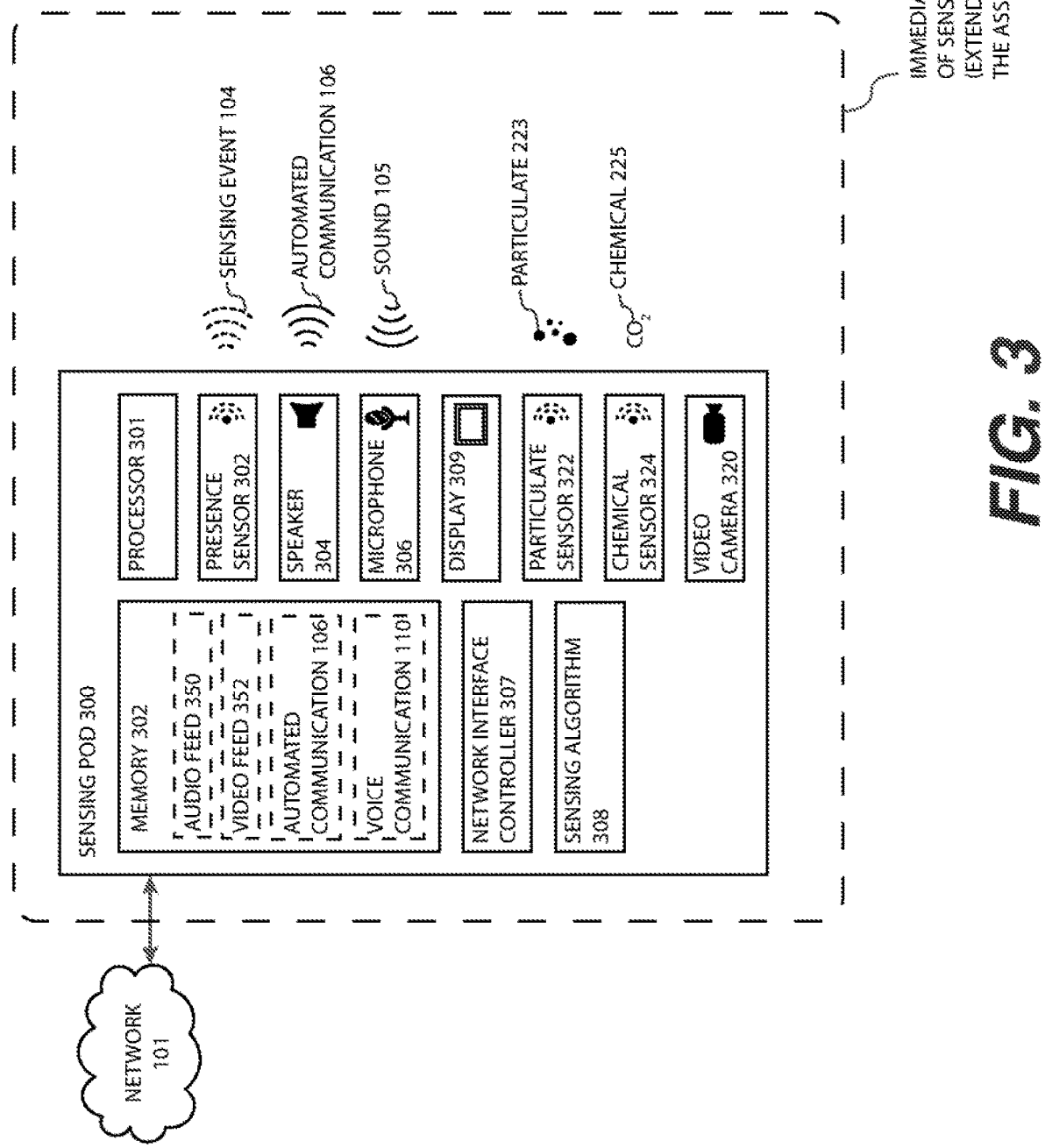
FIG. 3 illustrates a sensing pod that can be communicatively coupled to the assistance device of FIG. 2 to enable an extended environment for which the assistance device can perceive and/or communicate with the user, the sensing pod having its own immediate environment of the sensing pod and further including a capability to generate an audio feed with a microphone of the sensing pod and/or a video feed with a video camera of the sensing pod, according to one or more embodiments.

FIG. 3 illustrates a sensing pod 300 that can be communicatively coupled to the assistance device 200 of FIG. 2 to enable an extended environment 103 for which the assistance device 200 can perceive and/or communicate with the user 100, the sensing pod 300 having its own immediate environment 102 (e.g., the immediate environment 102B of FIG. 1) of the sensing pod 300, according to one or more embodiments. The immediate environment 102B may or may not overlap with the immediate environment 102A. Each component shown within the sensing pod 300 is connected to each other component of the sensing pod 300, for example through a data bus, wiring, or other data communication systems and methods.

In one or more embodiments, the sensing pod 300 may act as a less costly apparatus to extend a capability of the assistance device 200 to cover all or the most important and/or frequented areas of the caregiving environment. For example, within a caretaking environment there may be one instance of the assistance device 300 and a number of instances of the sensing pod 300 (e.g., one, five, twenty) communicatively coupled with the assistance device 200 through the network 101. In one or more embodiments, each sensing pod 300 and the assistance device 200 may have their network interface controller 207 and network interface controller 307, respectively, capable of interfacing with a wireless router (e.g., WiFi) that may form a local area network, with an additional connection between the assistance device 200 and a wide area network providing access to the rest of the assistance coordination network of FIG. 1. In one or more embodiments, the sensing pod 300 may powered by a battery.

As shown in FIG. 3 the sensing pod 300 includes a processor 301 and a memory 303. The sensing pod 300 may include the speaker 304 to generate automated communication 106 that may be received through the network 101 and/or the microphone 306 that may receive the sound 105 from the immediate environment 102 of the sensing pod 300 and either process a signal of the sound 105 at the sensing pod 300 or transmit the signal of the sound 105 to the assistance device 200. The sensing pod 300 may further include hardware components similar to the assistance device 200, including the presence sensor 302, the display 309, the video camera 320, the particulate sensor 322, and/or the chemical sensor 324. The network interface controller 307 may be a wireless transmitter-receiver, and may be able to form a mesh network between and among the assistance device 200 and each of the other instances of the sensing pod 300 within the caregiving environment.

The sensing algorithm 308 may function similarly to the sensing algorithm 208 or may be modified to better perform its function as part of the extended network 103 of the assistance device 200. For example, upon receive a signal from the presence senor 302 the sensing algorithm 308 may determine if the signal constitutes the sensing event 104, or the sensing algorithm 308 may merely determine whether the signal might qualify as a sensing event 104 and relay the signal to the assistance device 200 for determination by the sensing algorithm 208. As shown in the memory 303, the sensing pod 300 may buffer the audio feed 350, the video feed 352, and any automated communication 106 and/or voice communication 110.

FIG. 4 illustrates the automated assistance server 400 of FIG. 1 that may provide a general assistance to the user 100, according to one or more embodiments. For example, the general assistance may be a personal assistance for initiating a web search, ordering a product, engaging in a social interaction (either with an artificial intelligence assistant implemented in software and/or establishing a peer-to-peer connection with other instances of the user 100), schedule a reminder or event, control household connected devices and/or appliances (e.g., "internet of things" or "IoT" devices usable by the user 100 within a household), and similar functions. The automated assistance server 200 includes a speech recognition engine 460 to recognize and/or translate a speech of the user 100 and a personal assistance engine 462 that is a computer program for providing the personal assistance, carrying out actions at the request of the user 100, and for generating speech responses for the user 100. The speech recognition engine 460 may be software capable of identifying the sounds produced in human speech and/or capable of receiving and interpreting dictation. The speech recognition engine 460 may forward results of analysis to the personal assistance engine 462 to produce an appropriate response and/or induce an appropriate action according to a voice command protocol of the personal assistance engine 462. In one or more embodiments, the personal assistance engine 462 may provide an artificial intelligence assistant (e.g., Siri, Alexa, Google Assistant, Cortana, Bixby) and/or a robotic personality for interaction with the user 100. For example, the personal assistance engine 462 may feature a natural language user interface to answer questions, make recommendations, and perform actions by delegating requests to a set of web services. The personal assistance engine 462 may adapt to the user 100's individual language usage and individual searches (preferences) with continuing use, and may returns results that are individualized. In one or more embodiments, the personal assistance engine 462 may also be capable of music playback, making to-do lists, setting alarms, streaming podcasts, playing audiobooks, and providing weather, traffic, and other real time information, such as news. The personal assistance engine 462 may also be able to control several smart devices as the "brains" of a home automation system. In one or more embodiments not shown in the figures, the assistance device 200 may include a software component and/or client-side application for efficient communication and interfacing with the automated assistance server 400. Each component shown within the automated assistance server 400 is connected to each other component of the automated assistance server 400, for example through a data bus, wiring, or other data communication systems and methods.

The automated assistance server 400 includes a processor 401 on which computer executable instructions are processed and a memory 403. In addition, the automated assistance server 400 in one or more embodiments may include one or more instances of an assistance application 470 that is computer software that can perform specific instances of the assistance action 478 in response to a voice command of the user 100 (e.g., the initiation command 476) conforming to a voice command protocol 474 of the assistance application 470. In one or more embodiments, the assistance application 470 may be referred to as a "skill" of the automated assistance service (e.g., an Amazon Alexa Skill) that the user 100 may have to install or enable for use with the automated assistance service.

For example, the assistance application 470 may be a history application that may be able to tell the user 100 about historical events. The history application may have an invocation command 472, for example "launch history app." The voice command protocol 474 may be one or more commands that the history app recognizes and will response to. In this case, the voice command protocol 474 may include a number of commands such as "Tell me about another event from September 3rd" or "Hear more about this event" or "tell me about a famous battle in 1840". Each command acts as initiation command 476 conforming to the voice command protocol 474. The assistance application 470 may additionally require one or more voice inputs 480. For example, if the user 100 askes for "a famous battle" the assistance application 470 may request a voice input 480 of "in which year would you like to hear about a famous battle?" Similarly, for an assistance application 470 for ordering food delivery, an initiation command 476 may always request voice inputs 480 that include the menu items to be ordered and/or an address for delivery. Streamlined interactions involving the assistance application 470 between the assistance device 200, the automated assistance server 400, and the scheduling server 600 are further shown and described in conjunction with FIG. 6, FIG. 18 and FIG. 20.

Figure 5:
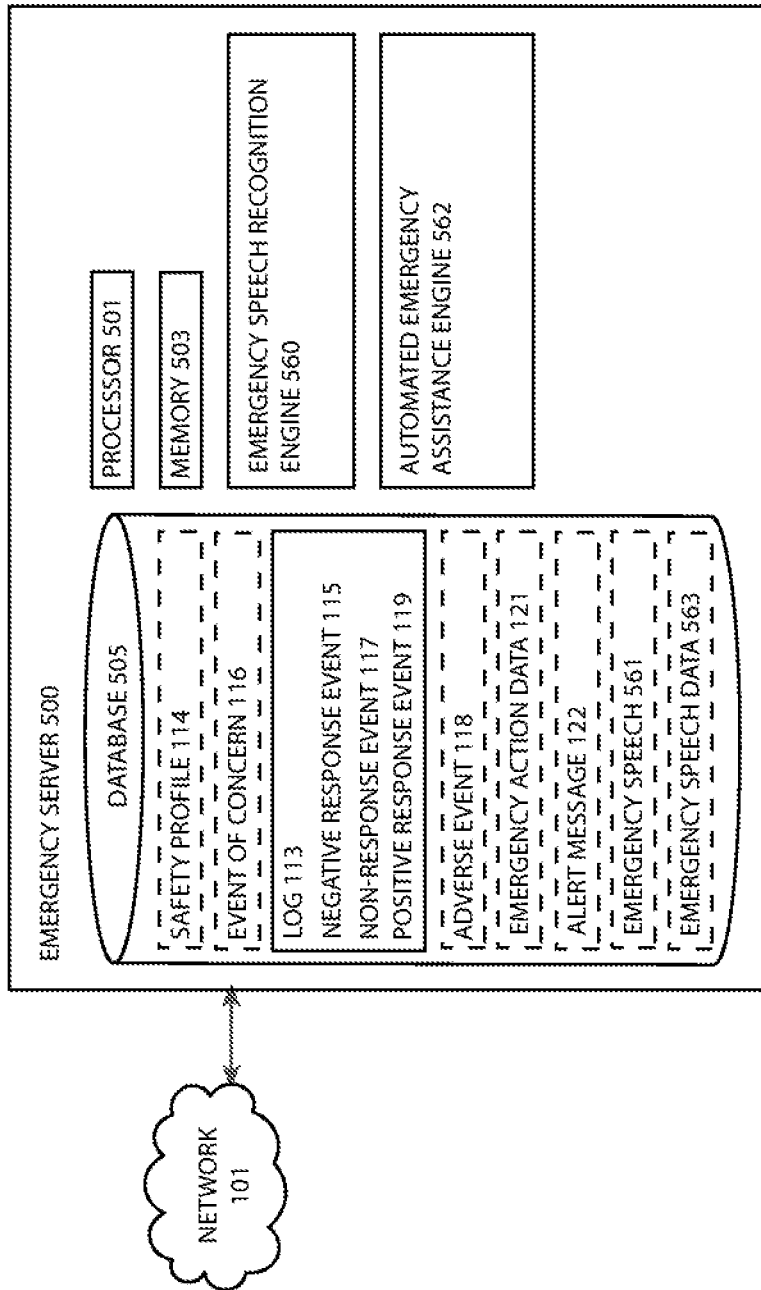
FIG. 5 illustrates the emergency server of FIG. 1 providing a specialized emergency assistance to the user (e.g., automatically connecting the user to the emergency service such as 9-1-1, providing an increase sensitivity to an emergency word, and/or aiding the user in determining a risk) rather than the general assistance service of the automated assistance server of FIG. 4, the emergency server including an emergency speech recognition engine to recognize and/or translate an emergency speech of the user (e.g., an emergency word such as "help" and/or a distressed voice tone), an automated assistance engine for providing the specialized emergency service to the user, and a database of the emergency server having the log of the events of concern and/or the adverse events, according to one or more embodiments.

FIG. 5 illustrates the emergency server 500 of FIG. 1 providing a specialized emergency service to the user 100 and/or capable of carrying out some of the functions shown and described in conjunction with the assistance application of FIG. 2, according to one or more embodiments. The emergency server 500 includes a processor 501, a memory 503, the database 505, and is connected to the network 101. Each component shown within the automated emergency server 500 is connected to each other component of the emergency server 500, for example through a data bus, wiring, or other data communication systems and methods.

The emergency speech recognition engine 560 may be similar to the speech recognition engine 460 but with enhanced and/or emphasized capability to recognize, interpret and/or identify an emergency speech 561 of the user 100. For example the emergency speech 561 may be: an emergency word such as "help!" (e.g., the emergency word 1110 of FIG. 11); a speech tone tending to indicate anxiety, pain, or suffering; and/or abnormally rapid, loud or incoherent speech. The emergency speech recognition engine 560 may also have a lower threshold for recognizing certain words commonly associated with danger or injury to the user 100, for example "medication", "dizzy", "injury", "smoke", expletives, and similar words. In one or more embodiments, the emergency speech recognition engine 560 may simultaneously receive the voice communication 110 of the user 100 at the same time as the speech recognition engine 460; however, upon meeting a threshold number of words associated with an emergency, danger or injury to the user 100 the automated emergency assistance engine 562 may communicate with the assistance coordinator 214 to route communications primarily to the emergency server 500 and/or initiate frequent instances of the status query 107 to the user 100.

The automated emergency assistance engine 562 is a software program that may provide a specialized emergency assistance to the user 100 and may provide an automated emergency assistance service. For example, the automated emergency assistance engine 562 may include procedures for affirmatively asking the user 100 if they are alright or if the user 100 needs assistance. Upon satisfaction of threshold conditions (for example, the automated emergency assistance engine 562 generates an automated communication 106 asking the user 100 if there is a fire and the user 100 responds "yes"), the automated emergency assistance engine 562 may first contact the emergency service 150 (e.g., call 9-1-1) and may additionally provide succinct instructions to the user 100 based on known factors to reduce risk to the user 100 under the circumstance until a live person associated with the emergency service (e.g., a 9-1-1 operator, a poison control specialist, a physician) may be connected through a two-way communication between the assistance device 200 and the device 700 of the emergency service 150.

The automated emergency assistance engine 562 may also take any additional emergency action 120, similar to those shown and described in conjunction with FIG. 1 and FIG. 2. For example, the automated emergency assistance engine 562 may generate the alert message 122 to transmit to the device 700B of the caregiver 130 and/or the device 700C of the emergency service 150. As shown in the embodiment of FIG. 5, the database 505 may store one or more instances of the safety profile 114, the log 113 (including without limitation the negative response event 115, the non-response event 116 and the positive response event 119), the event of concern 116, the adverse event 118, the alert message 122 and/or the emergency action 120. In one or more embodiments the assistance device 122 may transmit the voice communication 110 of the user 100 to the emergency server 500 for determination of the event of concern 116 and/or the adverse event 118 requiring the emergency action 120. In one or more other embodiments, the assistance device 200 may generate the adverse event 120 that may be communicated to the emergency server 500, which may in turn generate the alert message 122 and/or take additional instances of the emergency action 120. In yet one or more other embodiments, the assistance device 200 may determine one or more events of concern 116 and transmit the events of concern 116 to the emergency server 500 for determination of the adverse event 118. The emergency server 500 may also store as data what is determined by the emergency speech recognition engine 560 to be the emergency speech 561 of the user 100, and/or the emergency speech data 563 that may be a catalogue of reference emergency speech usable by the emergency speech recognition engine 560. The emergency speech data 563 may be unique to the user 100 or common to many instances of the user 100. If unique, the emergency speech data 563 may be stored in the safety profile 114 of the user 100.

FIG. 6 illustrates the scheduling server 600 of FIG. 1 including a processor 601, a memory 603, a database 605, and an assistance service scheduler 690 for streamlining, scheduling and/or enhanced communication and/or interaction with the automated assistance service provided by the automated assistance server 400. In one or more embodiments, a function of the scheduling server 600 is to pre-generate interactions with instances of the assistance application 470. For example, one routine may determine that at 6 PM on each weekday the user 100 will be asked via the assistance device 200 (and/or the sensing pod 300) whether the user 100 would like to order dinner. Upon an affirmative response by the user 100 the assistance service scheduler 690 may look up an assistance app identifier 692 with an associated invocation command 472 and look up the assistance action identifier 692 associated with an initiation command 472. In the restaurant application example above, the assistance app identifier 692 may be data that is a unique value specifying a pizza restaurant (e.g., Domino's Pizza), the invocation command 472 may be "order from Domino's," the assistance action identifier 692 may be a unique identifier associated with a particular command within the voice command protocol 474 of the pizza app, and the initiation command 472 may be "order pizza." While ordinarily the user 100 would be asked for additional voice inputs 480 in queries such as "please select a size" or "please select toppings" or "please provide delivery address", the voice inputs 480 may be pre-stored in the database 605 and communicated to the assistance application 470 following the initiation command 476. In this example, the user 100 did not have to remember to initiate the interaction to order dinner, did not have to remember the invocation command 472, did not have to remember the initiation command 476, and did not have to manually enter any repetitive or redundant instances of the voice inputs 480. From the experience of the user 100, they were asked if they would like dinner; the user 100 responded affirmatively; and the user 100 was then delivered a pizza to an address of the caregiving environment.

In one or more embodiments a custom command word 234 may be associated with the routine. For example the user 100 may specify "order me pizza" to mean run the entire routine for ordering a 10-inch Dominos peperoni pizza and delivering it to the address of the caregiving environment. The custom command word 234 may be stored as an audio file or a text file on the assistance device 200 and associated with a unique identifier matching a record on the scheduling server 600, the record comprising the assistance app identifier 692, the assistance action identifier 694, the invocation command 472, the initiation command 476 and/or one or more pre-stored voice inputs 480. The custom command word 234 may also be stored on the scheduling server 600 and the voice communication 110 of the user 100 relayed to the scheduling server 100 for determination of whether the voice communication 110 of the user 100 contains the custom command word 234.

In one or more embodiments, one or more of the voice inputs 480 can remain unspecified or be designated for a voice input from the user 100 at the time the assistance action is initiated. For example, where the user 100 moves between two caregiving environments a street address instance of the voice input 480 may remain unspecified and asked of the user 100 immediately following the initiation command 476 of the assistance application 470. The voice input 480 provided by the user 100 for the street address may also be utilized as a basis for an event of concern 116 or otherwise logged in the log 113. Each component shown within the scheduling server 600 is connected to each other component of the scheduling server 600, for example through a data bus, wiring, or other data communication systems and methods.

Figure 7:
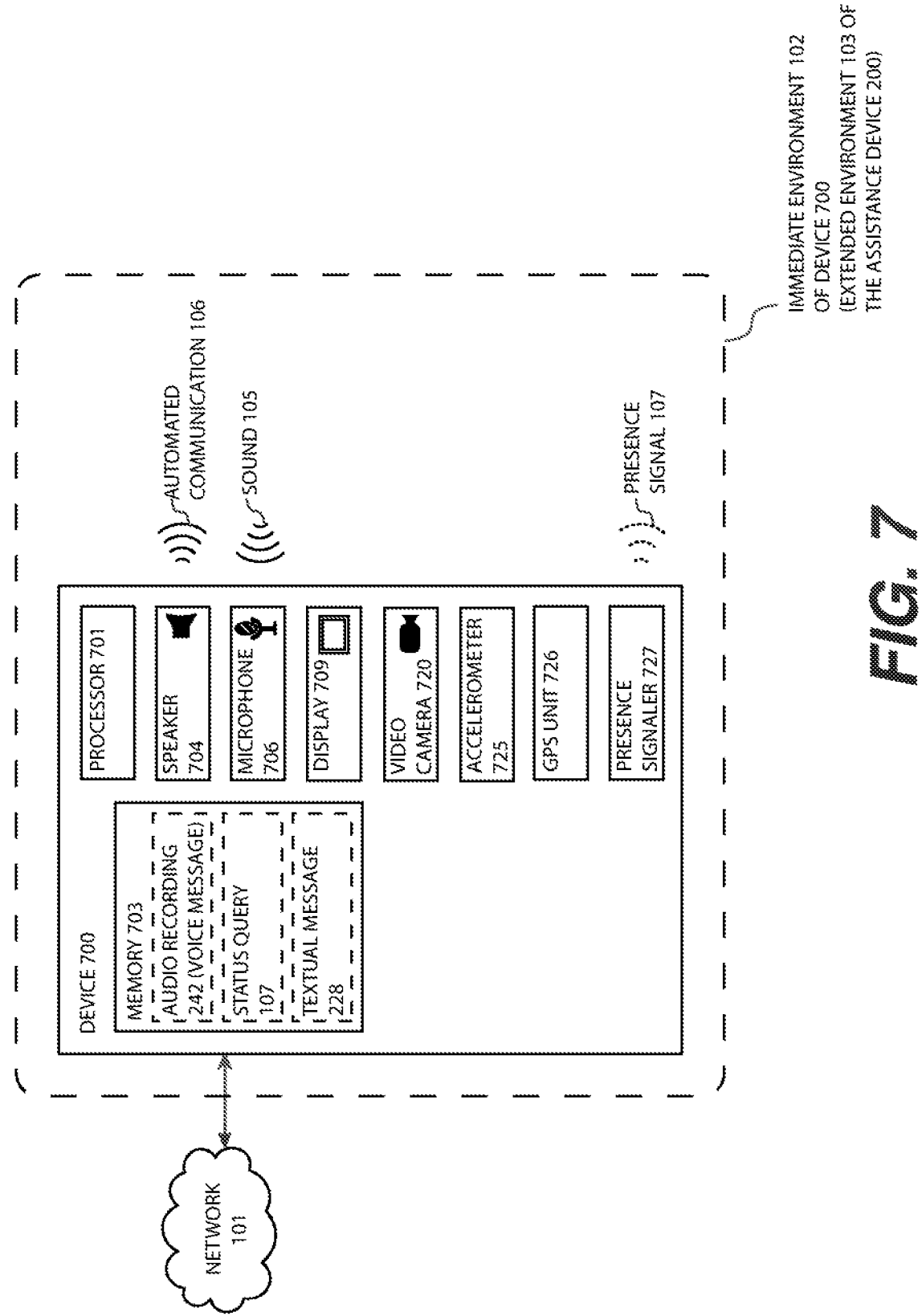
FIG. 7 illustrates the device of FIG. 1 of the user, the caregiver, and/or the emergency service, for example a mobile device, a tablet, a wearable device (e.g., a smartwatch, an electronic necklace with a panic button), a connected household device, and/or a desktop computer, the device of FIG. 7 including, for example, an accelerometer, a GPS unit, a presence signaler, a display, a speaker, a microphone, and a video camera, the speaker and the video camera usable to establish communication between and among devices of the user, of the caregiver, and/or of the emergency service as one of the one or more emergency actions coordinated by the assistance device of FIG. 1, according to one or more embodiments.

While the assistance device 200 may include each of the data shown and described in the database of 605 and carry out similar functions, in one or more embodiments the streamlined routines are stored on the scheduling server 600 and an initiation command 230 is utilized by the assistance device 200 to trigger the routine. FIG. 7 illustrates the device of FIG. 1 of the user 100, the caregiver 130, and/or the emergency service 150. The device 700 may be, for example, a mobile device (e.g., an iPhone, an Android phone, a Google phone, a Windows phone), a tablet (e.g., an iPad, a Galaxy, Amazon Fire), a wearable device (e.g., a smartwatch, an iWatch, a wristband tracking a vital sign, a necklace with a panic button), a connected household device, and/or a desktop computer. Each component shown within the device 700 is connected to each other component of the device 700, for example through a data bus, wiring, or other data communication systems and methods. The device of FIG. 7 includes the processor 701, the memory 703, the speaker 704, the microphone 706, the accelerometer 725, the GPS unit 726 and/or the presence signaler 727. The presence signaler 727 may generate a signal detectable by the presence sensor 202 of FIG. 2 and/or the presence sensor 302 of FIG. 3, according to one or more embodiments. For example the presence signaler 727 may be an RFID chip, a Bluetooth communications signal generator, or may generate an ultrasonic sound detectable by the assistance device 200 and/or the sensing pod 300. The video camera 720, the speaker 704, and/or the microphone 706 may be usable to establish communication between and among the user 100, the caregiver 130, and/or the emergency service 150 as one of the one or more emergency actions 120 coordinated by the assistance device 200. Data of the accelerometer 725 and/or the GPS unit 726 may be analyzed by the activity detection module 216. In one or more other embodiments, the device 700 does not include all components shown in FIG. 7: a desktop computer generally may not include the accelerometer 725.

Figure 8:
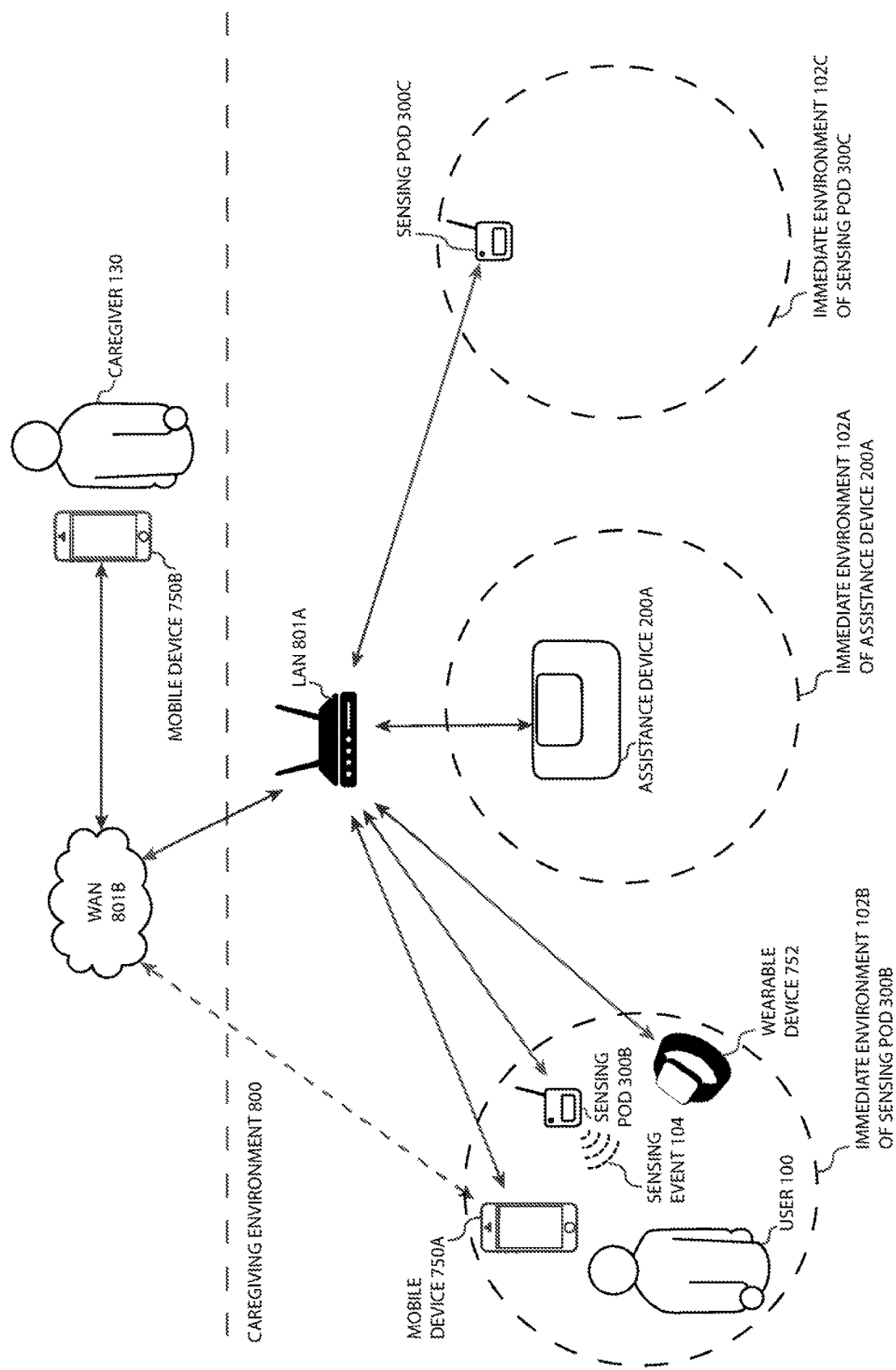
FIG. 8 illustrates a first caregiving environment network in which aspects of the assistance coordination network of FIG. 1 are deployed within and outside of a caregiving environment, a local area network (LAN) communicatively coupling the assistance device of FIG. 2 with two instances of the sensing pod of FIG. 3 to provide the extended network of the assistance device, the user and/or a device of the user sensed in a sensing event of a first sensing pod and an interaction of the user transmitted to the assistance device and a log comprising the interaction then transmitted to the mobile device of the caregiving of the user through a wide area network (WAN), according to one or more embodiments.

FIG. 8 illustrates aspects of the assistance coordination network of FIG. 1 deployed inside and outside of a caregiving environment 800 utilizing a local area network (LAN 801A) to communicatively couple the assistance device 200A, the sensing pod 300B and the sensing pod 300C, according to one or more embodiments. For example the caregiving environment 800 may be a home of the user 100, with the assistance device 200A placed in a kitchen, the sensing pod 300B placed in a hallway between a bedroom and a bathroom, and the sensing pod 300C placed in a living room, each connected to the other through the LAN 801 that may be a wireless router (e.g., connected using an 802.11 wireless communication protocol). The wireless router implementing the LAN 801A may then be connected to the WAN 801 (e.g., the internet) via an Ethernet cable and cable modem accessing an internet service provider (ISP). The assistance device 200A may have the immediate environment 102A (e.g., the kitchen), the sensing pod 300B may have the immediate environment 102B (e.g., the bedroom, hallway, and bathroom), and the sensing pod 300C may have the immediate environment 102C (e.g., the living room). Together, the immediate environment 102A, 102B and 102C may form the extended environment 103 of the assistance device 200A.

Figure 9:
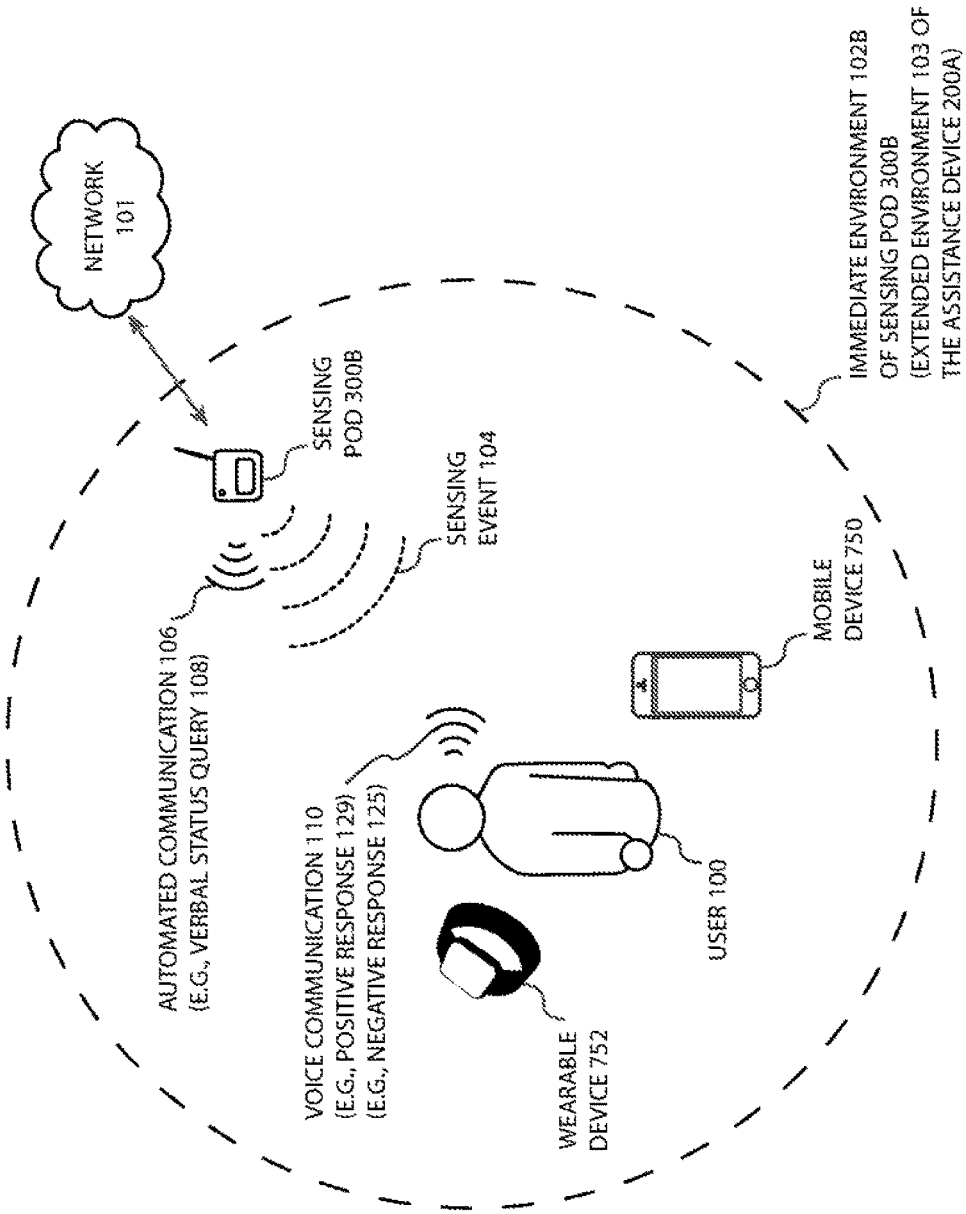
FIG. 9 illustrates a detailed view in which the interaction of FIG. 8 may occur in which the sensing pod determines a presence of the user through a sensing event, generates an automated communication such as a verbal status query to the user (e.g., "Isn't it a nice day? What do you think?"), and the user responds with a voice communication that may be a positive response (e.g., "Yes, it's nice out") or a negative response (e.g., "No", or "I don't care"), the positive response and/or the negative response determined by the assistance device and/or the emergency server to be a positive response event or a negative response event, respectively, which may be stored as data in the log for possible recordkeeping, analysis and/or communication to the caregiver and/or the emergency server, according to one or more embodiments.

In the embodiment of FIG. 8, the user 100 and/or a device 700 of the user 100 (e.g., the mobile device 750A, the wearable device 752) may be sensed in the sensing event 104 upon the user 100 nearing or entering the bathroom of the caregiving environment 800 and additional actions may be taken as shown and described in conjunction with FIG. 9. Periodically or upon occurrence of a specific event, the log 113 may be communicated from the assistance device 200A, through the LAN 801A and the WAN 801B to the device 700 of the caregiver 130 (e.g., the mobile device 750B). As shown in FIG. 8 the mobile device 750A may have an additional method of access to the WAN 801B, for example through a cell tower connection. In one or more alternative embodiments each of the components may be connected using a cellular data connection, for example 4G or LTE, or may even be connected through a satellite internet connection.

FIG. 9 illustrates a detailed view in which the interaction of FIG. 8 may occur in which the sensing pod 300B determines a presence of the user 100 within the immediate environment 120B through the sensing event 104. The sensing event 104 may be determined to be, for example, a noise made by the user 100 above a threshold environmental sound as gathered by the microphone 306, and/or by detecting a proximity of the mobile device 750A and/or the wearable device 752. In the embodiment of FIG. 9, the sensing pod 300B determines the sensing event 104 and calls the assistance device 200 which may return the voice status query 108 to the user 100 in the form of the automated communication 106. For example, the user 100 may be asked "Isn't it a nice day?, What do think?". The user 100 may respond with a negative response 125 (e.g., "No", or "I don't care") that may be determined to be the negative response event 115 and/or a positive response 129 (e.g., "Yes, it's nice out") that may be determine to be the positive response event 119. The negative response event 115 is an event of concern 116 that may logged in the log 113 and which may be immediately communicated to the caregiver 130 as shown and described in conjunction with FIG. 8.

Figure 10:
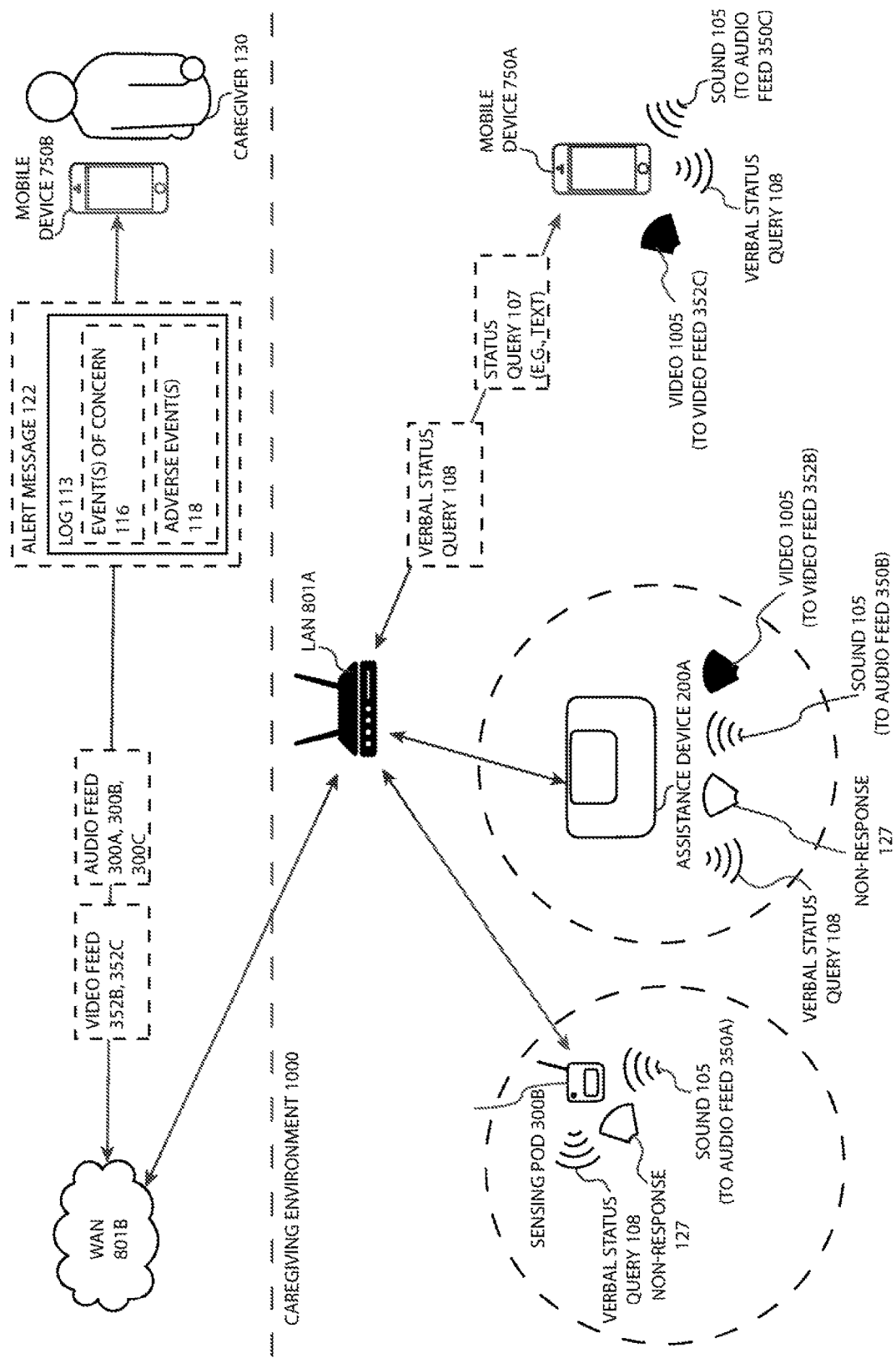
FIG. 10 illustrates a second caregiving environment network in which the verbal status query may be generated based on a factor other than the sensing event of FIG. 9, for example upon a threshold inactivity of the user, the sensing pod then receiving a non-response from its immediate environment, expanding the verbal status query and/or a status query that may be in a different medium to the mobile device of the user, logging a non-response event that may trigger an alert message to the mobile device of the caregiver, and/or establishing a video feed and/or an audio feed from the assistance device, the sensing pod, and/or the mobile device of the user to determine a state of the user within the caregiving environment, according to one or more embodiments.

FIG. 10 illustrates a second caregiving environment network (e.g., the caregiving environment 1000) comprising the assistance device 200A and the sensing pod 300B and demonstrating an instance of the emergency action 120 in response to the non-response event 117. Upon generation of the verbal status query 100 the assistance device 200A may initiate the countdown timer 212. In the embodiment of FIG. 10 the non-response 127 initially results in expansion of the status query 107 (e.g., a text message, a push notification) to the mobile device 750A. Additionally, a volume of the speaker 204 of the assistance device 200A and/or the speaker 304 of the sensing pod 300B may be raised and the verbal status query 108 repeated. Upon continuation of the non-response 127 the assistance device 200A may determine and log an event of concern 116 that is the non-response event 117. The assistance device 200A may reference the safety profile 114 of the user 100 to determine that a single non-response event 117 is an adverse event 118 requiring execution of two instances of the emergency action 120. First, the alert message 122 comprising the log 113 may be generated and communicated to the mobile device 750 of the caregiver 130. Second, a sound capture of the sound 105 and a video capture of the video 1005 may be initiated such that an the audio feed 350 and the video feed 352 may be automatically established to stream audio-visual footage from the speaker 304 of the sensing pod 300B, the video camera 320 of the sensing pod 300, the microphone 206 of the assistance device 200A, and/or the video camera 220 of the assistance device 200A. The caregiver 130 may also be able to engage in a two-way communication through the speakers of the sensing pod 300B and/or the assistance device 200A to initiate real-time voice communication with the user 100.

Figure 11:
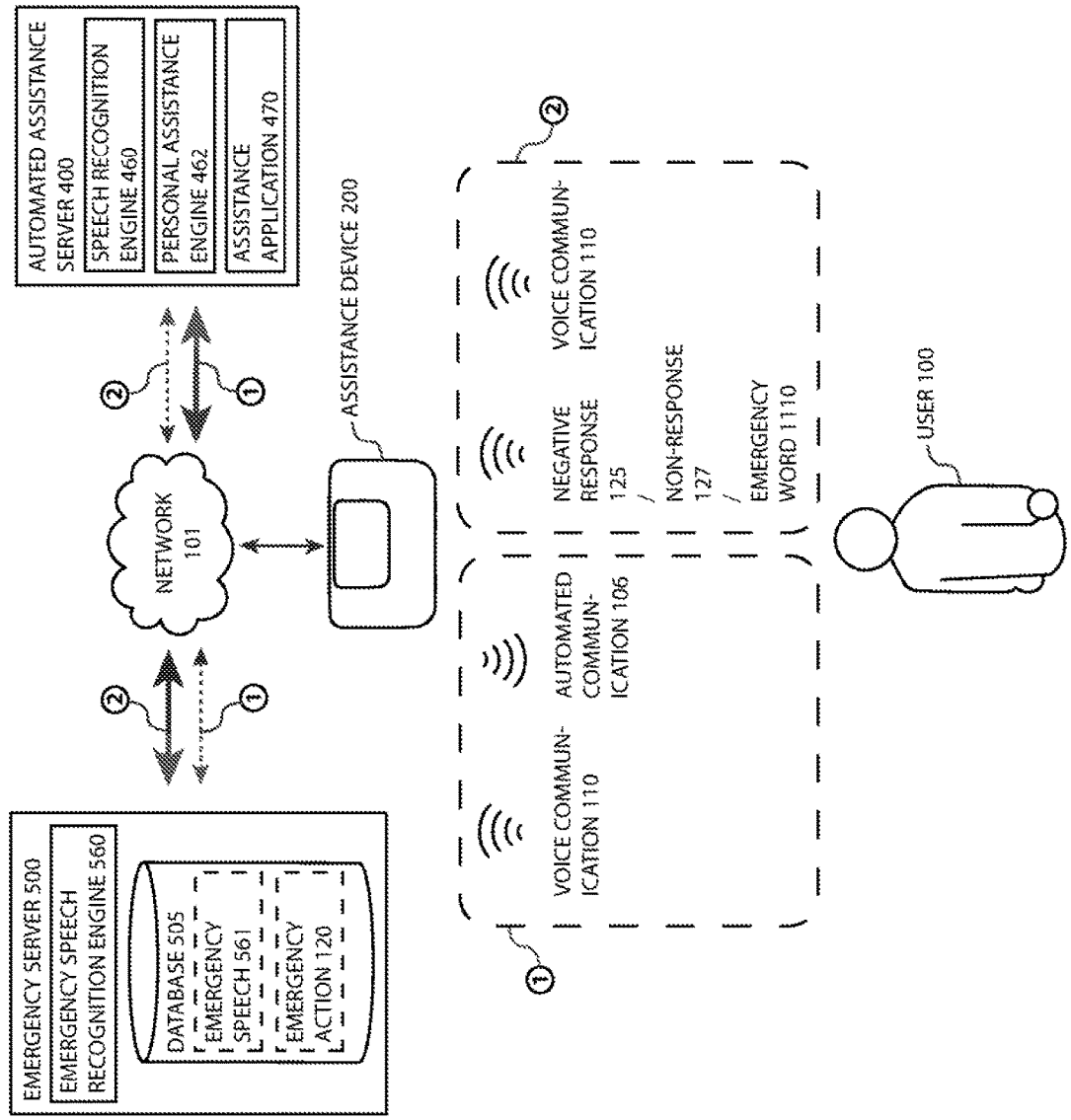
FIG. 11 illustrates a routing of a voice communication of the user between the automated assistance server of FIG. 4 providing the general assistance and the emergency server providing of FIG. 5 providing the specialized emergency service, a voice communication of the user that relates to the general assistance (e.g., "what time is the game on?") routed to the automated assistance server, whereas the voice communications of the user following an event of concern, an adverse event, and/or upon recitation of certain verbal commands (e.g., "Help") routed to the emergency server by the assistance coordinator of FIG. 2, according to one or more embodiments.

FIG. 11 illustrates a routing of a voice communication 110 of the user 100 between the automated assistance server 400 of FIG. 4 providing the general assistance and the emergency server 500 providing of FIG. 5 providing the specialized emergency service. At a first time, labeled 'circle 1' in FIG. 11, the user 100 engages in ordinary, non-emergency voice commands and speech with the assistance device 200. For example, the user 100 may ask what the weather will be like tomorrow, or ask what time a particular sports game will be on television. The automated assistance server 400 running the personal assistance engine 462 may provide automated communication 106 responsive to the questions of the user 100. During this first time most speech may be communicated to the automated assistance server 400 but only some speech may me transmitted to the emergency server 500 (e.g., for occasional analysis to determine an emergency speech pattern). However, during a second time designated 'circle 2', the assistance service coordinator 214 of FIG. 2 may determine that communications (e.g., the voice communication 110) are to be re-routed primarily to the emergency server 500, for example to evaluate the voice communication 110 based on the emergency speech recognition engine 560. As shown in FIG. 11, the re-routing may occur because of a negative response 125 of the user 100, a non-response 127 and/or recitation of an emergency word 1110. As an example, the user 100 may have fallen during a shower and despite the sensing pod 300 being near the bathroom the user 100 may be outside of an ordinary audible range of the sensing pod 300. However, after a non-response event 117, more subtle sounds may activate voice analysis and communications may be re-routed to the emergency server 500 which may utilize the emergency speech recognition engine 560 that may have an increased sensitivity to detect the emergency word 1110 of the user 100 stuck in the shower.

Figure 12:
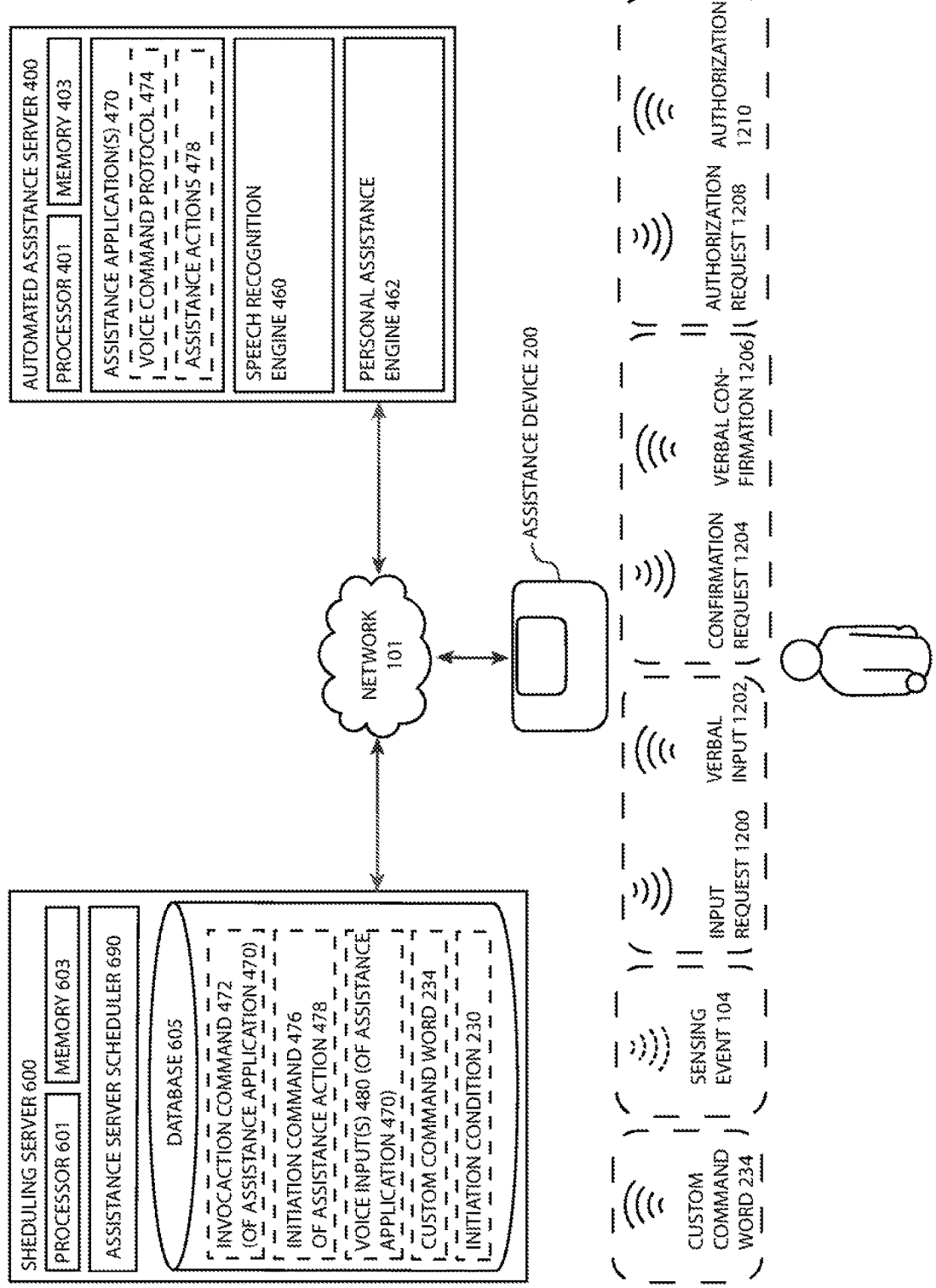
FIG. 12 illustrates numerous capabilities of the scheduling server of FIG. 6 to ease interaction with the automated assistance service and provide an opportunity for determining events of concern, the capabilities including but not limited to: invocation of an assistance application and/or initiation of an assistance action of the assistance application via a custom command word; initiation of the assistance action and/or assistance application upon an initiation condition such as a predetermined time or upon a sensing event within a timeframe (e.g., asking the user if they would like dinner ordered from a delivery service if they are sensed entering a kitchen between 5 PM and 7 PM); reducing verbal inputs required from the user to initiate an assistance action; and initiating a confirmation request and/or an authorization request before executing the assistance action and/or the assistance application, according to one or more embodiments.

FIG. 12 illustrates numerous capabilities of the scheduling server 600 of FIG. 6 to ease interaction with the automated assistance service and provide an opportunity for determining events of concern 116. The assistance action 478 can be initiated upon occurrence of an initiation condition 230. In one or more embodiments, the initiation condition 230 may be the user 100 speaking a custom command word 234. For example, the custom command word 234 when recited at the assistance device 200 may automatically trigger the scheduling server 600 to initiate the assistance action 478 according to a streamlined, pre-defined routine. The assistance action 478 may also be triggered by the sensing event 104. For example, the initiation condition 230 may include multiple aspects that must occur simultaneously (e.g., the user 100 sensed in the living room and the sensing event 104 occurring between 4 PM and 7 PM on a week night).

The scheduling server 600 and/or the automated assistance server 400 may generate one or more input requests 1200 for additional voice inputs 480 required before completing execution of the assistance action 478. The user 100 may respond to the input request 1200 with the verbal input 1202. Finally, data in the scheduling server 600 and/or the assistance device 200 may indicate that before execution of the assistance action 478 that the user 100 is provided with a confirmation request 1204 to which the user 100 must provide the verbal confirmation 1206 and/or the user 100 is provided with the authorization request 1208 to which the user 100 may reply with the authorization 1210 to satisfy the authorization request 1208. Either the confirmation request 1204 and/or the authorization request 1208 may be provided to the user 100 before the invocation command 472 and/or the initiation command 476 has been transmitted to the automated assistance server 400. In addition, the user 100 and/or the caregiver 130 may utilize a web interface or a mobile app to adjust and set routines and associated instances of the initiation condition 230.

Figure 13:
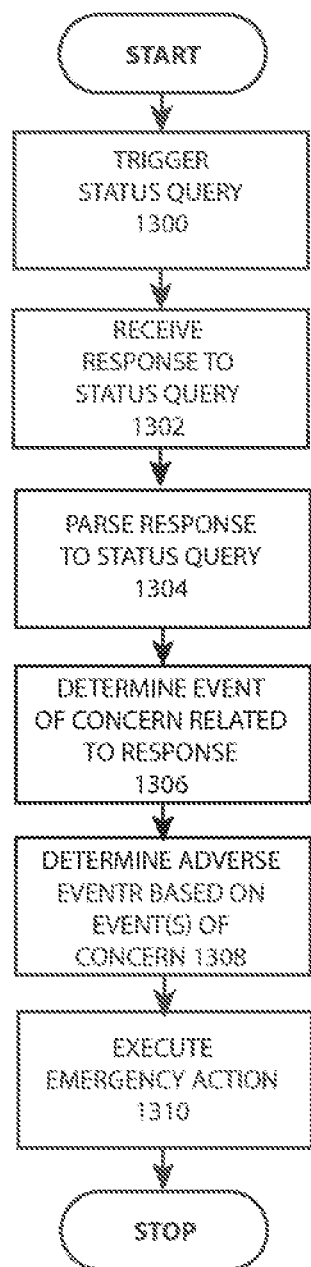
FIG. 13 is a monitoring and assistance process flow that illustrates one aspect of the assistance coordination network of FIG. 1 in which a status query is triggered, a response to the status query is parsed to determine an event of concern, the event of concern is determined to arise to the level of an adverse event possibly based on previous events of concern, and an emergency action is initiated, according to one or more embodiments.

FIG. 13 is a monitoring and assistance process flow that illustrates one basic function of the assistance coordination network of FIG. 1, according to one or more preferred embodiments. Operation 1300 triggers a status query 107 usable to elicit a response from the user 100 for analysis, the response likely usable to determine a state, a disposition, a feeling, an emotion, a condition (e.g., physical, mental, psychological, and/or emotional) or a status of the user 100. For example, the status query 107 may be: a textual message (e.g., the textual message 228) that can be presented on a display (e.g., the display 209, the display 309, the display 709 as a text message or push notification) and/or a graphical user interface on the display; a symbol or an emoji presented on the display (e.g., a smiley face or sad face that a user 100 may press on a touch screen display); and/or the verbal status query 108 generated by a speaker of the assistance device 200, the sensing pod 300, and/or the device 700 of the user 100 (e.g., the speaker 204, the speaker 304, and/or the speaker 704). Operation 1302 receives a response to the status query 107 in a form that may be the same or different than the format in which status query 107 was generated and/or delivered to the user 100. In one or more embodiments, the format may be the same in both the transmission and the receipt. For example, for a status query that is in the form of a textual message 228 to the mobile device 750 of the user 100, the user 100 may response with a text message (e.g., the user 100 types "yes fine" on a keyboard of the mobile device 750). In one or more other embodiments, the status query 107 and the respond to the status query may be in a different format. For example, in response to the verbal status query 108 the user 100 may be presented with faces having various expressions on the display 209. In such case the user 100 may only need to touch the appropriate facial expression to generate the response that may be determined to be an event of concern 116. However, in one or more other embodiments, the "response" received may be the non-response 127, for example an ambient sound of the immediate environment 102 or no touch input.

Operation 1304 parses the response to the status query 107 received in operation 1302. Operation 1304 prepares data that may be used to determine the event of concern 116. For example operation 1304 may receive and format a sound signal (e.g., from the sound 105 and/or the voice communication 110), may utilize the speech-text converter 218 to generate a text string or other data representing the voice communication 110, or other formatting processes required to turn raw audio into data usable by an algorithm.

Operation 1306 determines whether the response of the user 100 is a negative response 125 (e.g., resulting in a determination of the negative response event 115), a non-response 127 (e.g., resulting in a determination of the positive response event 117), and a positive response 129 (e.g., resulting in a determination of the negative response event 119). Operation 1308 determines an adverse event 118 has occurred based on the event of concern 116 and/or one or more previous instances of an event of concern 116, the adverse event 118 triggering one or more instances of the emergency action 120. Operation 1308 may reference a rule for determining when the event of concern 116 arises to the adverse event 118. In one or more embodiments, the rule may be static (e.g., a set rule for an adverse event 118) that any event of concern 116 is an adverse event 118 and the rule may be stored locally on a device that carried out process 1302. In one or more other embodiments, a safety profile 114 may be referenced, the safety profile 114 including rules and/or conditions under which the event of concern 116 is an adverse event 118. For example, the safety profile 114 may specify that any negative response event 115 resulting from data gathered from a particular instance of the sensing pod 300 (e.g., the sensing pod located near a stairway where the user 100 may trip) may be determined to be an adverse event 118. Operation 1308 may also determine the emergency action 120 to be taken in association with the adverse event 118, such as sending an alert message 122 to the device 700 of the caregiver 130 and/or establishing a two-way communication between the device 700 of the emergency server 500. Operation 1308 may determine the emergency action 120 to be taken by referencing the safety profile 114 to determine an applicable instance of the emergency action data 121, the referencing and/or extracting the instance of the emergency action 121 and reading its contents to determine how to specifically execute the emergency action 120.

Operation 1310 executes an emergency action 120. For example, operation 1310 may follow instructions specified in the emergency action data 121 to extract data from a log 113 to generate a second instance of the log 113 for communication to the device 700 of the caregiver 130, the second instance including a subset of data determined relevant to the adverse event 118. In one instance, a third consecutive instance of the non-response event 117 may trigger the emergency action 120 of sending the alert message 122, but all three instances of the non-response event 117 may be communicated in the log 113 within the alert message 122 sent for communication to the device 700B of the user 100 in the alert message 122.

Figure 14:
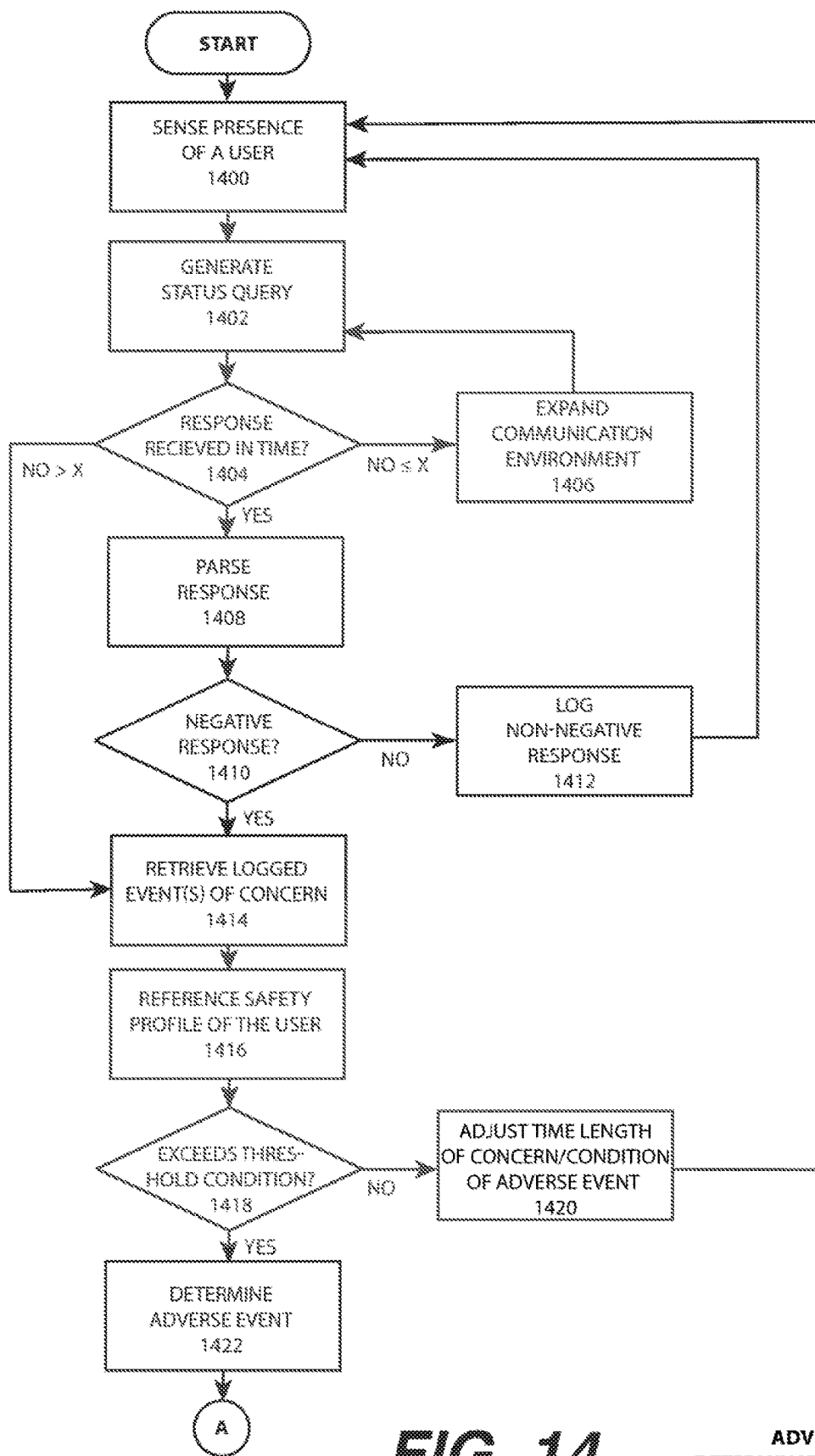
FIG. 14 is an adverse event determination process flow illustrating additional aspects of the process flow of FIG. 13, additionally including expansion of a communication environment (e.g., a communication related to an immediate environment of a sensing pod expanded to an extended environment including all sensing pods, assistance devices, and/or devices of the user within the caregiving environment of FIG. 8), logging non-negative responses, and adjusting conditions under which the event of concern and/or adverse event is determined, according to one or more embodiments.

FIG. 14 is an adverse event determination process flow illustrating more detailed aspects of the process flow of FIG. 13, according to one or more embodiments. Operation 1400 demonstrates a specific initiation of the status query 107 based on sensing the presence of the user 100. Specifically, the presence sensor 202 and/or the presence sensor 302 may sense the user 100 with an immediate environment 102 of the presence sensor 202 and/or an immediate environment of the presence sensor 302. Similarly, the device 700 may sense the presence of the user 100 within an immediate environment 102 of the device 700 through one or more sensors of the device 700 such as the accelerometer 725 (in the case of the accelerometer 725, the device 700 may primarily detect actual physical contact of the user 100 with the device 700). In one or more alternate embodiments, a different initiator of the status query 107 may be used, for example if a sensor detects a sound spike and a vibration spike within the immediate environment 102 of the sensor which may indicate that the user 100 has fallen down or collided with an object. Operation 1402 generates a status query (e.g., the status query 107, the voice status query 108) that may be an audible and/or a visual communication intended for the user 100. Operation 1404 may initiate a countdown timer 212 set to a time length. There may be a value 'X' set to a number of attempts to communicate the status query 107 to the user 100. Where no response is received within the time length, operation 1406 may increment a data counter and attempt to expand the status query 107 into one or more additional devices that can communicate and/or receive communications from the user 100 (e.g., the assistance device 200, the sensing pod 300, the device 700 of the user). Operation 1402 may then re-generate the status query 107 in the expanded environment (which may be, for example, the extended environment 103 of FIG. 1). If the counter exceeds the value of attempts (e.g., the 'X' value in FIG. 14), then operation may proceed to operation 1414. However, where operation 1404 receives a signal (e.g., a text message reply, a voice response of the user 100, the user 100 pressing a button) then received data of the response is passed to operation 1408 which parses the response.

In one or more embodiments operation 1408 parses the response locally on an apparatus that generated the status query 117 (e.g., the assistance device 200) or the response may be parsed in a remote location accessible over the network 101, for example the emergency server 500 (e.g., which may be a cloud computing server). In some instances, the data may be in a readily usable format, for example a text string from the mobile device 750 of the user 100. In other cases the response may require additional analysis. For example, the voice communication 110 may require analysis by the speech recognition engine 460 and/or the emergency speech recognition engine 560. In one or more operations not shown in the embodiment of FIG. 14, any parsed data determined not likely to be from the user 100 may return the process flow to operation 1406.

Operation 1410 analyzes the response to see if it is a negative response (e.g., the negative response 125) which may result in a determination and storage of a negative response event 115. For example, the verbal response of the user 100 may be matched to known words associated with a negative state, for example "No," "Bad", "Poor"; a small combination of words such as "Not well"; and/or a phrase "I have been better." In one or more embodiments, each verbal status query 108 may have associated specific known words of negativity (e.g., when asking how a specific ailment or injury of the user 100 is doing such as a knee injury the verbal status query 108 may have associated a data that will determine "inflexible" to be a negative response event 115). In one or more other embodiments the tone of the user 100, the cadence of the user 100, or additional voice analysis techniques may be used to determine that even where an event may include positive content (e.g., "yes, I'll be ok") that additional indicators may be concerning. Although not shown, operation 1410 may also determine the positive response event 119 through similar methods.

If a negative response event 115 is not determined, operation 1410 proceeds to operation 1412 that may log the non-negative response event, a neutral response, and/or a positive response event 119. Where a negative response event 115 is determined (and/or where operation 1404 exceeded a threshold number of attempts to determine a non-response event 117), operation 1414 may reference and/or retrieve previous instances of the event of concern 116. For example, the safety profile 114 and/or the log 113 of the user 100 may store each instance of the non-response event 117 and each instance of the negative response event 115 which has occurred over in a period of time (e.g., a day, a week, a month, since implementation of the assistance coordination network). One or more of these previous events of concern 116 may be utilized in an evaluation of whether the adverse event 118 has occurred. In one or more alternative embodiments, process 1414 may be excluded and the event of concern 116 determined in process 1404 and/or 1410 may be the only event of concern 116 evaluated. For the purposes of a specific example of the embodiment of FIG. 14, a number of previous events of concern 116 within a time period (e.g., any non-response event 117 within an eight hour period) may be extracted.

Operation 1406 references the safety profile 114 to determine a threshold condition to compare the number of previous events of concern 116 and the recent event of concern 116 generated in operation 1404 and/or 1414. For example, the safety profile 114 may specify an adverse event 118 where: (i) any two consecutive instances of the non-response event 116, and/or (ii) the two instances of the negative response event 115 followed by one instance of the non-response event 117 and/or (iii) any four instances of the non-response event 117 or the negative response event 115 within an eight hour period. Operation 1418 determines whether the event of concern 116 generated in operation 1404 and/or operation 1414, plus any relevant events of concern 116 extracted from the log 113 and/or the safety profile 114, exceed the threshold condition specified in the safety profile 114. Where the threshold condition is not met (e.g., only one event of concern 116 occurring within the time period where a high number is specified), operation 1418 proceeds to operation 1420. Operation 1420 may make one or more adjustments to the safety profile 116 and/or additional data impacting the determination of the event of concern 116 and/or the adverse event 118. For example, operation 1420 may adjust the time length of the timer of operation 1404 or cause operation 1402 to occur more frequently. Additionally, in one or more embodiments operation 1420 may update the safety profile 114 to add, remove, or modify a threshold condition upon where one or more events of concern 116 will be determined to be an adverse event 118.

In the specific example of the embodiment of FIG. 14, a total of four instances of the event of concern 116 has occurred within an eight-hour period. Operation 1418 compares the four instances of the event of concern 116 to the threshold in the safety profile 114. Upon determination of the exceeded threshold condition, Operation 1422 determines the adverse event 118 that requires an additional urgent action beyond merely logging the event of concern 116. Specifically, the adverse event 118 determination 1422 may require execution or more emergency actions 120. The adverse event determination process flow of FIG. 14 is continued in FIG. 15.

Figure 15:
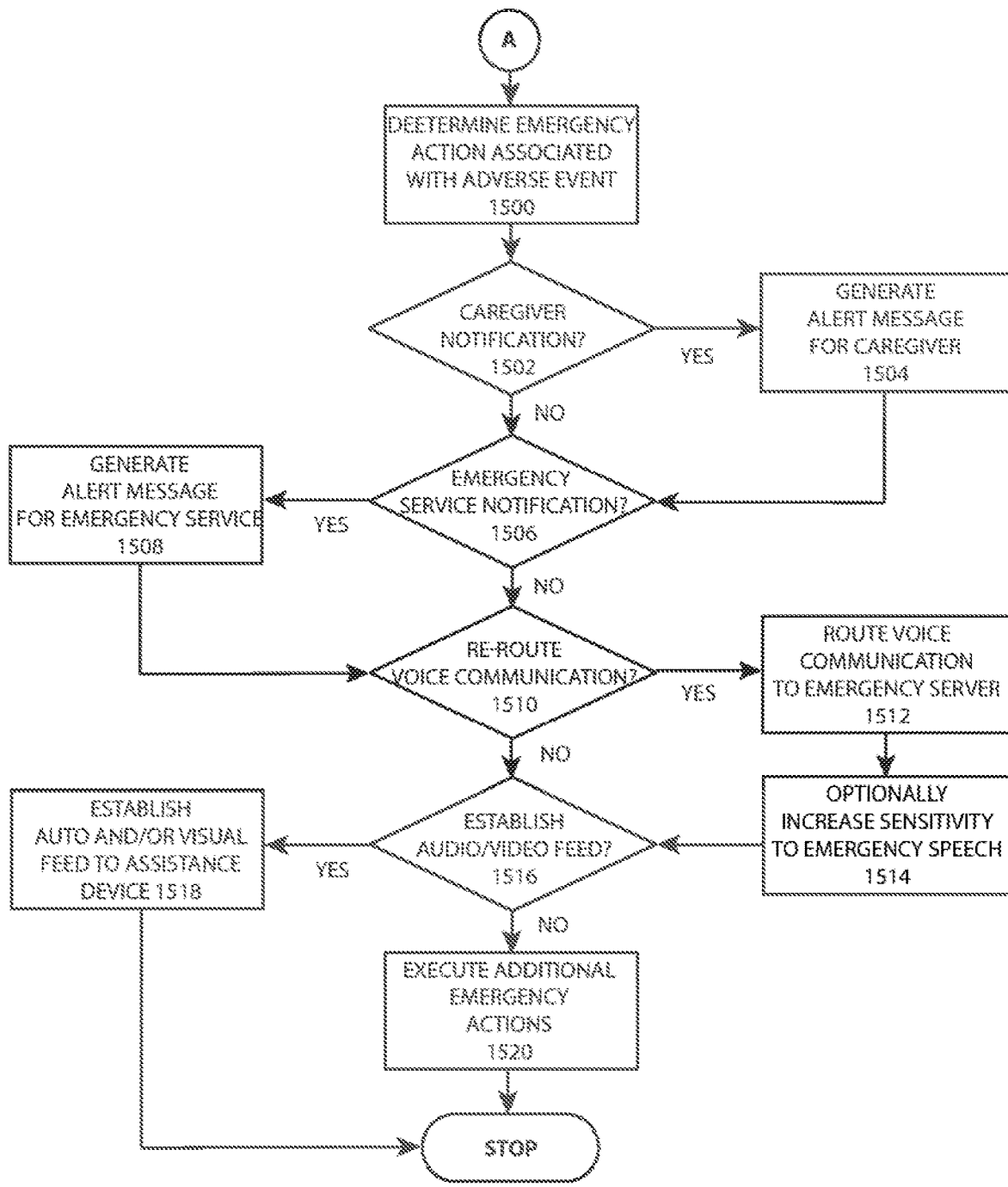
FIG. 15 is an emergency action process flow illustrating one or more emergency actions taken in response to determination of the adverse event of FIG. 14, including but not limited generating an alert message for the caregiver of the user and/or the emergency service, routing a voice communication of the user to the emergency server of FIG. 5, increasing a sensitivity to an emergency speech, establishing an audio and/or video feed to establish communication with the user, and/or execution of additional emergency actions, according to one or more embodiments.

FIG. 15 is an emergency action process flow illustrating one or more emergency actions of FIG. 13 taken in response to determination of the adverse event of FIG. 14, according to one or more embodiments. The process flow of FIG. 15 is continued from operation 1422 of FIG. 14.

Operation 1500 determines one or more emergency actions 120 associated with the adverse event 118. The safety profile 114 may specify which of one or more emergency actions 120 should occur under what circumstances, e.g., the safety profile 114 may be referenced by operation 1500 to determine implicated emergency actions 120. The emergency action data 121 data defined and/or specifies how a specific instance of the emergency action 120 should executed. Operation 1502 determines whether a device 700 of caregiver 130 of the user 100 is to be notified as an emergency action 120. If so, operation 1504 generates an alert message 122 for the caregiver 130 and that may be transmitted to the device 700 of the caregiver 130 after extracting contact data (e.g., a phone number, an email address, a unique identifier of a mobile app user profile or ID associated in a mobile app database). For example, the caregiver 130 may be notified by a text message, an automated voice call, an email, and/or a message on a mobile application (e.g., "mobile app"). The alert message 122 may include numerous pieces of information, such as the log 113 of instances of the event of concern 116 giving rise to the adverse event 118, a GPS coordinate of a mobile device 750 of the user 100, and/or data from connected household devices of the user 100 (e.g., which lights are currently turned on in the caregiving environment). In either determination of operation 1502, operation 1502 may proceed to a next determination of the emergency action 120, for example operation 1506 which may make a similar determination as operation 1502 but for notification to the emergency service 150. The emergency action process flow then proceeds to operation 1510 which determines if voice communications of the user 100 (e.g., the voice communication 110) should be re-routed to the emergency server 500. If so, operation 1512 may replicate or re-route any voice communication 110 of the user 100 to the emergency server 500 and optionally increase sensitivity to an emergency speech (e.g., the emergency speech 561), for example, by utilizing the emergency speech recognition engine 560. Although not shown, gain of a signal received may also be increased and/or a threshold for receiving sound signals may be reduced, for example to be able to transmit what may be a feint sound of a user 100 who has fallen just on the edge of an immediate environment 102 of the device with a microphone (e.g., the microphone 206, the microphone 306, the microphone 706). Operation 1516 determines whether an audio and/or video feed should be established between the device 700 of the caregiver 130 and one or more devices capable of monitoring and/or communicating with the user 100 (e.g., the assistance device 200, the sensing pod 300, the device 700 of the user 100, and/or other devices within the caregiving environment such as a connected television with a web cam). If such a feed is to be established, operation 1518 establishes a connection between devices and begins streaming the audio feed (e.g., the audio feed 350) and/or the video feed (e.g., the video feed 352) to the device 700 of the caregiver 130 and/or the device 700 of the emergency service 150.

Although not shown in the embodiment of FIG. 15, a two-way communication channel may be established in a similar way. In addition, emergency actions 120 may depend upon an outcome of a previous emergency action 120. For example, if an automated call to a phone of a first caregiver 130A is unsuccessful, a second call may be placed to a second caregiver 130B. Where the assistance device 200 and/or the sensing pod 300 include the display 109 an image of the caregiver 130 may be displayed as recorded by the device 700 of the caregiver 130. Finally, operation 1520 may take any additional emergency actions 120 that may be specified and may act as a continuation of the emergency action 120 process flow of FIG. 15 accordant to a similar pattern shown and described. An example may be to turn on all of the internet-connecting lighting and turn off all music on a network-connected stereo within the caregiving environment to aid emergency services.

Figure 16:
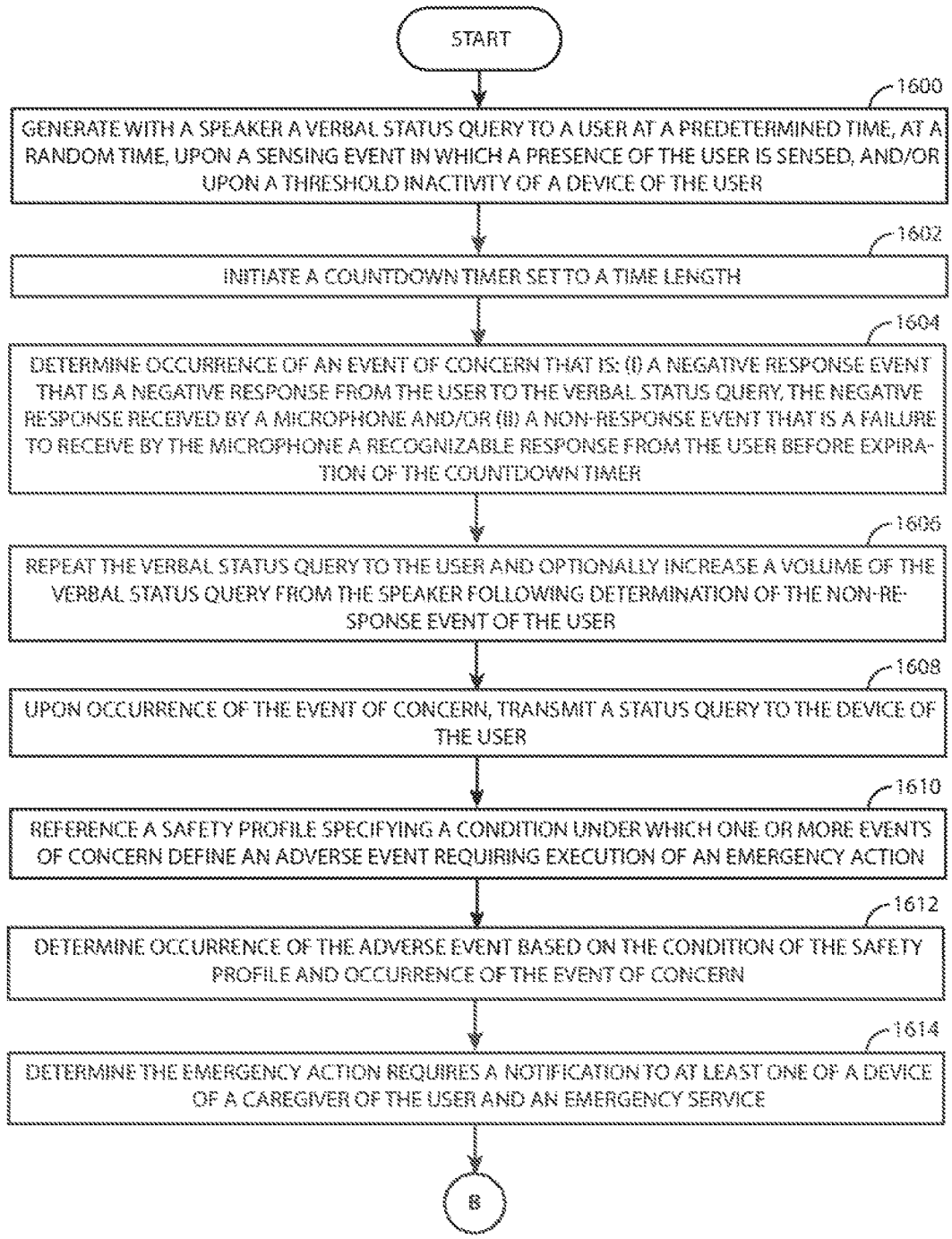
FIG. 16 illustrates additional aspects and one specific example of the determination of the adverse event, according to one or more embodiments.

FIG. 16 illustrates additional aspects and one specific example of the determination of the adverse event 118, according to one or more embodiments. Operation 1600 generates with a speaker (e.g., the speaker 204, the speaker 304, the speaker 704) a verbal status query 108 to a user 100 at a predetermined time, at a random time, upon a sensing event 104 in which a presence of the user 100 is sensed (e.g., by the presence sensor 202, the presence sensor 302), and/or upon a threshold inactivity of a device 700 of the user 100. The verbal status query 108 is an automated communication 106. The predetermined time may be, for example, once every three hours, three times per day, or at 7 AM and at 5 PM (depending on a monitoring need of the user 100). In one or more embodiments, a caretaker 130 may adjust the schedule of the predetermined time and/or the random time. Operation 1602 initiates a countdown timer 212 set to a time length, for example 1 minutes, 20 seconds, or 3 seconds. The length of time may be set for an expected response of the user 100 relative to the verbal status query 108. For example, where the verbal status query 108 is "explain what you ate today", the countdown timer 212 may be set such that enough time is allowed for the user 100 to consider their response. Operation 1604 determines occurrence of an event of concern 116 that is: (i) a negative response event 115 that is a negative response 125 from the user 100 to the verbal status query 108, the negative response 125 received by a microphone (e.g., the microphone 206, the microphone 306) and/or (ii) a non-response event 117 that is a failure to receive by the microphone a recognizable response from the user 100 before expiration of the countdown timer 212. The failure to receive the recognizable response may occur, for example, because no signal is received, no substantial signal is received (e.g., no sound above a threshold ambient noise), or because a speech recognition software (e.g., the speech recognition engine 460) could not determine a speech pattern or word. Operation 1606 repeats the verbal status query 108 to the user 100 and optionally increase a volume of the verbal status query 108 from the speaker following determination of the non-response event 117 of the user 100. Operation 1606 may also reduce volume of household connected devices such as a television or stereo.

Operation 1608, upon occurrence of the event of concern 116, transmits a status query 107 to the device 700 of the user 100 (e.g., a text message sent to a mobile device 750 of the user 100, a push notification set to a connected television of the user 100). Operation 1610 references a safety profile 114 specifying a condition under which one or more events of concern 116 define an adverse event 118 requiring execution of an emergency action 120. Operation 1612 then determines occurrence of the adverse event 118 based on the condition of the safety profile 114 and occurrence of the event of concern 116, e.g., by comparing the one or more events of concern 116 to the conditions in the safety profile 114. Operation 1614 determines the emergency action 120 requires a notification to at least one of a device 700 of a caregiver 130 of the user 100 and an emergency service 150. The process flow of FIG. 16 is continued in the process flow of FIG. 17.

Figure 17:
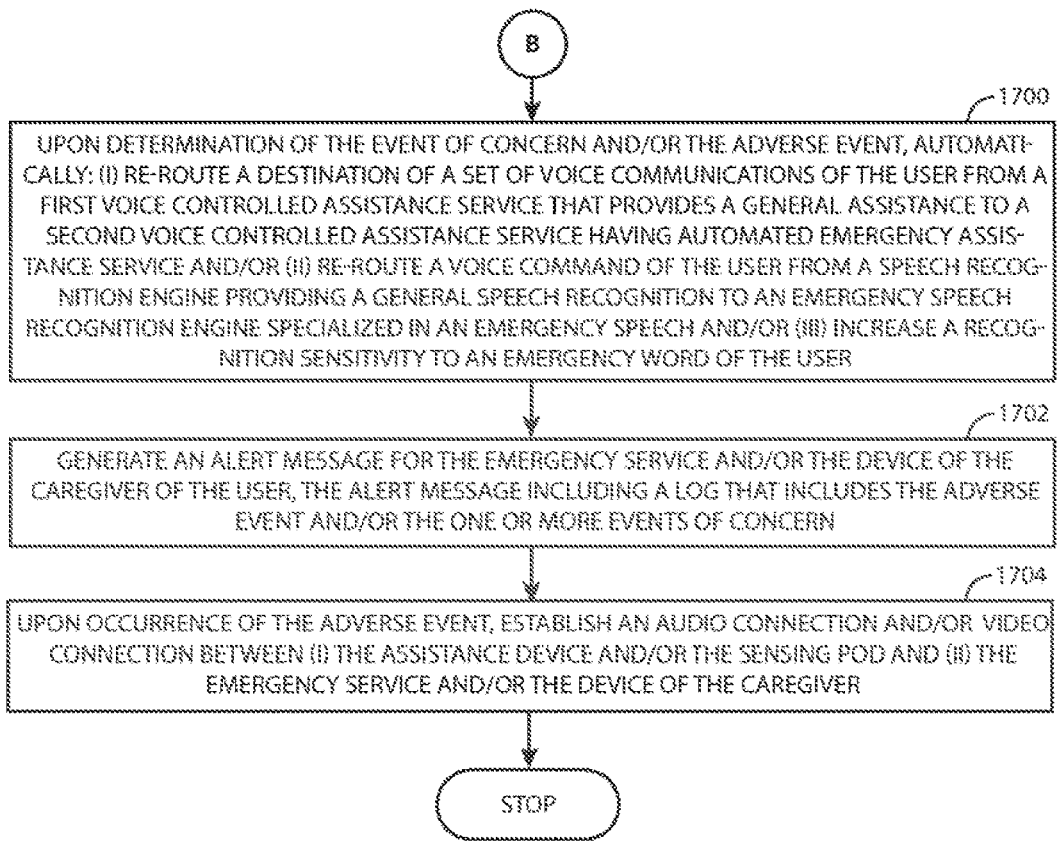
FIG. 17 illustrates additional aspects and one specific example of the determination of the emergency action, according to one or more embodiments.

FIG. 17 illustrates additional aspects and one specific example of the determination of the emergency action 120, according to one or more embodiments. Operation 1700, upon determination of the event of concern 116 and/or the adverse event 118, takes any combination of the following three actions automatically which may be specified in one or more instances of the emergency action data 121. First, operation 1700 may re-route a destination of a set of voice communications 110 of the user 100 from a first voice controlled assistance service that provides a general assistance (e.g., provided by the automated assistance server 400) to a second voice controlled assistance service having automated emergency assistance service (e.g., provided by the emergency server 500). Second, operation 1700 may re-route a voice command of the user 100 from a speech recognition engine 460 providing a general speech recognition to an emergency speech recognition engine 560 specialized in recognizing an emergency speech 561. Third, operation 1700 may increase a recognition sensitivity to an emergency word (e.g., the emergency word 1110) of the user 100. Operation 1702 generates an alert message 122 for the emergency service 150 and/or the device 700 of the caregiver 130 of the user 100, the alert message 122 including a log 113 that includes the adverse event 118 and/or the one or more events of concern 116. Finally, operation 1704, upon occurrence of the adverse event 118, establishes an audio connection (which may be the audio feed 352) and/or video connection (which may be the video feed 352) between (i)

an assistance device 200 and/or a sensing pod 300 and (ii) the emergency service 130 and/or the device 700 of the caregiver 130.

In addition to initiating an emergency action 120 in monitoring the user 100, the assistance coordination network of FIG. 1 also serves a number of related functions such as streamlining use of the automated assistance service. This encourages the user 100 to adapt to and engage with the automated assistance server 400 and therefore the assistance device 200 along with the assistance coordination network and/or its elements. As a result, there may be increased opportunity to monitor, evaluate and/or protect the user 100 from the standpoint of the caregiving organization, the caregiver 130, the emergency service 150, and/or the user 100.

FIG. 18 is an assistance application automation process flow illustrating automated interaction with an assistance application 470 and an assistance action 478 of the assistance application 470 conforming to a voice command protocol 474, according to one or more embodiments. Operation 1800 selects an assistance application 470 of a voice controlled assistance service along with an assistance action 478 of the assistance application 470, the assistance action 478 conforming to a voice command protocol 474 of the assistance application 470. The assistance action 478 may be initiated by a command. For example, a thesaurus application may be invoked via the automated assistance server by saying "Launch Thesaurus." The assistance action 478 may be a command "Synonym for", followed by a word. Operation 1802 pre-specifies one or more voice inputs 480 required upon initiation of the assistance action 478 to execute the assistance action 478 of the assistance application 470, the one or more voice inputs 480 conforming to the voice command protocol 474 of the assistance application 470. For example, where a given assistance action 478 will request a voice input 480, the voice input 480 may be pre-recorded and/or pre-stored to be provided to the assistance application 470 without affirmative action by the user 100.

Operation 1804 optionally specifies: (i) a confirmation requirement for a verbal confirmation of the user 100 (e.g., the confirmation request 1204 of FIG. 12) prior to execution of the assistance application 100 and/or (ii) an input request 1200 for one or more additional inputs (e.g., one or more instances of the verbal input 1202 of FIG. 12) conforming the voice command protocol 474 before execution of the assistance application 470. Operation 1806 schedules execution of the assistance action 478 of the assistance application 470 and/or a condition for execution associated with the assistance action 478 (e.g., the initiation condition 230). For example, the user 100 or the caregiver 130 may specify that an assistance application 470 that orders food for the user 100 is scheduled to run each evening at 5 PM, or when an inactivity of the user 100 is sensed by the assistance device 200 (e.g., by the activity detection module 216).

Operation 1808 determines occurrence of the condition associated with the assistance action 478 of the assistance application 470 of the voice controlled assistance service. Operation 1810 initiates a verbal confirmation (e.g., the confirmation request 1204) of the user 100 prior to execution of the assistance application 470 and/or initiates an input request 1200 for one or more additional inputs 480 conforming the voice command protocol 474 before execution of the assistance application 470. One instance of the condition may be occurrence of a time scheduled in operation 1806. Operation 1812 transmits an invocation command 472 of the assistance application 470 and the one or more voice inputs 480 required for execution of the assistance action 478. Alternatively, Operation 1812 may transmit an instruction (e.g., the initiation instruction 232) for the assistance device 200 to initiate the assistance action 478 through the invocation command 472 of the assistance application 470 and the one or more voice inputs 480 required for execution of the assistance action 478. In one or more alternative embodiments, the assistance device 200 may provide the instruction to begin streamlined usage of the assistance application 470 to the scheduling server 600, or the scheduling server 600 may provide the instruction to begin streamlined usage of the assistance application 470 to the assistance device 200, depending on where appropriate invocation commands 472, initiation commands 476 and/or voice inputs 480 are stored as data.

FIG. 19 is a customizable command process flow illustrating the automation of the assistance action 478 of FIG. 18 utilizing a custom command word 234, according to one or more embodiments. Operation 1900 defines a custom command word 234 and associates the custom command word 234 with an assistance application 470 of a voice controlled assistance service along with an assistance action 478 of the assistance application 470, the assistance action 478 conforming to a voice command protocol 474 of the assistance application 470. The custom command word 234 for example may be "need lenses" to automatically order contact lenses to the user 100's address using existing payment details. Otherwise, the user 100 may have to remember an exact invocation command 472, e.g., "Open Clear-View Eye Care Products", and go through a workflow within the voice command protocol 474 each time the user 100 wants to order contact lenses from their preferred supplier. Operation 1902 pre-specifies one or more voice inputs 480 required upon initiation of the assistance action 478 to execute the assistance action 478 of the assistance application 470, the one or more voice inputs 480 conforming to the voice command protocol 474 of the assistance application 470.

Operation 1904 specifies: (i) a confirmation requirement for a verbal confirmation of the user 100 prior to execution of the assistance application 470 and/or (ii) a requirement for an input request 1200 for one or more additional voice inputs 480 conforming the voice command protocol 474 before execution of the assistance application 470. Operation 1906 receives the custom command word 230 to trigger the assistance action 478 of the assistance application 470 of the voice controlled assistance service. Operation 1908 functions similarly to operation 1810 of FIG. 18, and operation 1910 functions similarly to operation 1812 of FIG. 18. Finally, operation 1912 generates a speech reply (e.g., an instance of the automated communication 106) and/or an action executed in response to the assistance action 478 initiated and assistance application 470 invoked. The action executed may be, for example, to control a household connected device such as dimming a lightbulb or turning off a connected television.

FIG. 20 is an adverse event calibration process flow illustrating adjustment of the determination of the adverse event 118 requiring an emergency action 120 in response to the determination of an event of concern 116 and/or an adverse event 118, according to one or more embodiments. Operation 1202 determines occurrence of an event of concern 116 that is: (i) a negative response event 115 that is a negative response 125 from the user 100 to the verbal status query 108, the negative response 125 received by a microphone (e.g., the microphone 206, the microphone 306, the microphone 706), and/or (ii) a non-response event 117 that is a failure to receive by the microphone a recognizable response from the user 100 before expiration of the countdown timer (e.g., the countdown timer 212). Operation 2002 decreases the time length to which the countdown timer is set based on a previous occurrence of one or more events of concerns 116 within a predetermined timeframe. For example, a user 100 may by default have one minute to respond before expiration of the countdown timer 212 but, after one or more events of concern 116 the countdown timer 212 may drop to ten seconds. Operation 2004 adjusts the condition under which one or more events of concern 116 define the adverse event 118 requiring execution of an emergency action 120 based on the previous occurrence of one or more events of concern 116 within the predetermined timeframe. For example, where a first event of concern 116 may trigger an alert message 122 to a first caregiver 130 that may be a professional caregiver, a second consecutive event of concern 116 may trigger the alert message 122 to four additional instances of the caregiver 130 that may be family members. Finally, operation 2006 adjusts a frequency of status queries (e.g., the status query 107) based on the occurrence of the one or more previous events of concern 116 within the predetermined timeframe. For example upon occurrence of the non-response event 117, instances of the status query 107 may increase in frequency from once per four hours to once per thirty minutes, possibly until a positive response event 119 occurs.

The assistance coordination network may also engage in heightened monitoring of the caregiving environment through additional sensors that may detect vitals of the user, an environmental hazard to the caregiving environment and/or a health risk to the user 100. FIG. 21 is a personal vitals and environmental hazard emergency action process flow illustrating detection of an environmental hazard by the assistance device 200 of FIG. 2 and/or the sensing pod 300 of FIG. 3 and/or adverse personal vitals from a wearable instance of the device 700 (e.g., a smartwatch that can determine a heartrate), according to one or more embodiments. Operation 2100 may detect an environmental hazard or adverse vital, for example by receiving a signal from a particular sensor (e.g., the particulate sensor 222, the particulate sensor 322, or even a particulate sensor 722 not shown in the embodiment of FIG. 7) and/or a chemical sensor (e.g., the chemical sensor 225, the chemical sensor 324, or even a chemical sensor 724 not shown in the embodiment of FIG. 7). The particulate sensor 223 may be able to sense a particulate 223 such as smoke, smog, vapor, dust and additional particulate. In one or more embodiments the particulate sensor 223 is a smoke detector that detects smoke. The chemical sensor 234 may be able to detect a chemical 225 such as an oxidizing agent, a reducing agent, carbon dioxide, carbon monoxide, cyanide gas, ammonia, oxygen (including lack of or over abundance of oxygen), ozone, nitrous oxides, sulfurous oxides, volatile organic compounds, and similar hazardous molecules. The vitals may include, for example, a heartbeat, a blood pressure, a temperature of the user 100, a blood oxygen level, a blood glucose level, and other medical data derivable from the wearable device and/or non-wearable devices within the caregiving environment communicatively coupled to the assistance device 200.

In the embodiment of FIG. 21, operation 2102 automatically determine an adverse event 118 upon completion of operation 2100. Operation 2104 generates a warning within the caregiving environment (e.g., the caregiving environment 800 of FIG. 8). For example the assistance device 200 may broadcast to all communicatively coupled sensing pods 300 through a LAN 801A a warning that could be a siren (e.g., similar to a smoke alarm siren) or may be an instance of the automated communication 110 instructing the user 100 to get to safety. Operation 2106 and operation 2108 operate substantially similarly to operation 1504 of FIG. 15 and operation 1508 of FIG. 18, respectively. However, the alert message 122 within a context of an environmental hazard may be communicated though more urgent means (e.g., a persistent automated phone call or communications to all known devices 700 of the caregiver 130). Similarly, operation 2110 through operation 2120 are similar to operation 1510 through operation 1520 of FIG. 15.

FIG. 22 is a user message process flow illustrating a process by which the user 100 may store an away message 244 suspending a generation of one or more verbal status queries 108 and providing notice to the caregiver 130, according to one or more embodiments. Operation 2200 stores an away message 244 of the user 100, wherein the away message 244 is an audio recording 242 of the user 100. For example, the away message 244 may be recorded as the audio recoding 242 directly on the assistance device 200, or may be recorded on the device 700 of the user 100 (e.g., via a mobile app on a mobile device 750 of the user 100). Operation 2002 then associates an expected inactivity time 240 with the away message 244 of the user 100. For example the away message 244 may state that the user 100 has gone to visit a neighbor, and the user 100 may select (e.g., on a user interface) an expected inactivity time 240 of one hour. The audio recoding 242 and/or the expected inactivity time 240 may be communicated to a server through the network 101 (e.g., stored on the emergency server 500) or may be stored on the assistance device 200. Operation 2204 optionally adjusts the condition under which one or more events of concern 116 define the adverse event 118 requiring execution of the emergency action 120 based the expected inactivity time 240. For example, instances of the status queries 108 may continue but what may ordinarily be determined to be an event of concern 116 may not be considered an event of concern 116 as long as the expected inactivity time 240 has not expired. Additionally, operation 2206 suspends instances of the verbal status query 208 until expiration of the expected inactivity time 240. Operation 2208 determines expiration of the expected inactivity time 240. Operation 2210 generates with a speaker a verbal status query 108 to a user 100 at expiration of the expected inactivity time 240. In one or more embodiments the audio recoding 242 containing the away message 244 can be delivered to the device 700 of the caregiver 130 upon creation, upon a check-in by the caregiver 130 (e.g., where the caregiver 130 uses the device 700 to "ping" the assistance device 200 for the log 113), any time the user 100 sets an expected inactivity time 240 of greater than one hour, and/or other similar circumstances.

FIG. 23 is an interaction of concern process flow illustrating a status query 108 that may be in the form of a question, a puzzle, a quiz, and/or a trivia to determine a cognitive ability of the user 100 including determination of an event of concern 116 for an incorrect and/or a non-responsive answer, according to one or more embodiments. Operation 2300 generates information that may be of interest to the user 100, for example a trivia related to the user 100's generation of birth (e.g., a popular culture trivia from a 1950's era). In another example, operation 2300 may invoke a history application to provide an assistance action 478 of describing something that occurred on this date in history. An affirmative response from the user 100 may be solicited to ensure the user 100 heard and understood the information of interest. Operation 2302 waits a period of time, for example 24 hours, before taking further action. Operation 2304 generates a question, a puzzle, or a trivia question related to the information of interest, which acts as the status query 108 that may be used to determine a status of the user 100. For example, the question may be "who was the famous president you learned about yesterday?". In one or more alternate embodiments, operation 2304 may also begin the process flow without a need for quizzing and/or testing on information previously provided. For example, operation 2304 may test basic math or facts (e.g., "what year is it?"). Operation 2306 receives a response of the user 2306 and parses the response similar to operation 1408 of FIG. 14. Operation 2308 determines whether the response received is correct and/or responsive to the question of operation 2304. The correct answer may be treated as a positive response event 119 and an incorrect answer (or a non-responsive or incoherent answer) may be treated as a negative response event 115. Correct answers may be stored as data either as a text string, a number, an audio file to be compared to a response of the user 100, and/or other data type, and may then be associated with a particular instance of the status query 108. Additionally, a scoring system may be used depending on how the degree to which the answer is correct, relevant, and/or response.

Upon determination of a correct and/or responsive answer, operation 2310 may log the answer and/or any score, for example in the log 113 as a positive response event 119. Optionally the correct answer along with one or more other answers may be provided to the device 700 of the caregiver 130 in operation 2312. On the other hand, where an incorrect and/or non-responsive answer is provided, operation 2314 through operation 2322, similar to 1414 through 1422 of FIG. 14, may be utilized to determine whether the incorrect answer is an adverse event 118. In one or more embodiments, events of concern 116 related to quizzes and puzzles may be stored, tracked, and determined separately relative to events of concern 116 related to state-based negative responses 125 of the user (e.g., "I don't feel well") or a non-response event 117.

An example embodiment of the assistance coordination network will now be described. Dorothy is an eighty-two-year-old widow living in a suburban neighborhood. Dorothy has a daughter living in a nearby city, Anne, and a professional hospice social worker who checks up on Dorothy once per week and helps her do errands such as buy groceries. Dorothy wants to continue to live in her home where she has lived for thirty years. However, Dorothy gets very lonely and Anne worries she does not have enough mental stimulation or social engagement. She also has numerous health issues and has taken several falls in the last year. Anne and the professional hospice worker are concerned. Dorothy has a necklace with a button that will notify emergency services, but she often takes it off and forgets to put it back on.

To help monitor Dorothy and provide opportunity for intuitive engagement with technology Anne and the hospice worker install an assistance hub (e.g., the assistance device 200) in Dorothy's home. They install the assistance hub the kitchen, and three "pods" (e.g., the sensing pod 300) throughout the house, including in Dorothy's bathroom where she has slipped before. The pods and the assistance hub communicate with one another through Dorothy's WiFi network. Anne and the social worker also preselect applications (e.g., the assistance application 470) that Dorothy can use to order food or control her television. They help her to schedule applications and set custom commands so that a single word (e.g., the custom command word 234) can trigger an entire action of an application even where it would normally require numerous voice interactions, commands or inputs.

Dorothy engages with the assistance coordination network daily. The hub asks her how she is doing at 8 AM after it senses her entering the kitchen. Around 5 PM it also asks whether she would like to order dinner from one of her favorite three restaurants. Dorothy can reliably communicate with the hub from her kitchen and some parts of adjacent rooms when the doors are open, forming the immediate environment of the hub (e.g., the immediate environment 102 of the assistance device 200). The pods, each with their own immediate environment for communication, allow Dorothy to be in contact with the hub and additional elements of the assistance coordination network in almost any part of her house, forming an extended communication environment of the hub (e.g., the extended environment 103).

Dorothy has some good days and challenging days, including some occasional memory loss. Dorothy's responses are compiled into a log (e.g., the log 113) that is sent to Anne and the social worker every day. They have pre-selected some status queries (e.g., the status query 107) that relate to Dorothy's condition, for example her frequent hip pain. When Anne notices Dorothy is not responding well to queries about Dorothy's hip generated by the hub Anne is provided the opportunity to call to remind Dorothy to elevate her leg and take her medication.

One day Dorothy decides to do some gardening in her backyard. She has had some vertigo earlier in the morning. When asked by the hub how she was doing at 8 AM, Dorothy responded "I'm feeling dizzy." The hub logged Dorothy's response as a negative response (e.g., a negative response event 117) but at that point the response did not arise to a level considered an adverse event (e.g., the adverse event 118) based on Dorothy's profile in the hub (e.g., the safety profile 114). However, the hub utilized its computer instructions to alter its procedure so it would attempt to check in with Dorothy again in a few hours rather than wait until 5 PM.

Dorothy gardens for an hour and then returns to the house. When entering the utility room to wash up she slips. She cannot get to her feet and thinks she may have broken a bone. Anne is likely busy at work and only calls every other day, and the social worker just visited Dorothy two days before. Dorothy does not have her emergency necklace on because she did not want to get it dirty when gardening.

At 11 AM the pod in the nearby living room generates a status query: "How are you feeling, Dorothy?" Dorothy hears the pod and shouts to it: "Bad. Help!" A microphone captures Dorothy's voice, and converts it to an audio signal. A voice recognition system on the hub and/or in a remote cloud computer linked to the hub through the internet (e.g., the emergency server 500) recognizes the words of the speech. The hub references the log and determines that Dorothy had previously generated an event of concern earlier in the day. Dorothy's safety profile indicates that any two consecutive events of concern are an adverse event requiring the hub take an emergency action. Dorothy's safety profile indicates the emergency action under these circumstances is to notify both Anne and the social worker on their cell phones. Second, Dorothy's safety profile indicates that any two consecutive events of concern result in re-routing of communication from an automated assistance server providing a general assistance to an emergency server providing a specialized emergency assistance.

Anne and the social worker each receive a text message specifying that Dorothy had a negative response event at 8 AM (including text of Dorothy's response to the hub) and that she had a non-response event at 11 AM. The social worker is in a meeting and does not immediately see the message. Anne however, does see it. She selects an option on a mobile app of her mobile device to begin an audio-video feed from the hub and each of the pods. She cannot seem to see Dorothy but does hear something. Anne leaves work immediately but is several hours away. Anne calls Dorothy's phone line but there is no answer.

The hub broadcasts an audible warning through each pod that Anne and the social worker have been notified to let Dorothy know help may be on the way. Dorothy yells for help again. This time, the hub picks up an emergency word. The specialized emergency server (e.g., utilizing the emergency speech recognition engine 560) determines "help" with an increased sensitivity, even though Dorothy's speech is strained due to pain. The emergency server automatically calls to 9-1-1 and opens a two-way communication between the microphone/speaker of the pod and the emergency service personnel (e.g., the emergency service 150). Emergency services arrive shortly after and take Dorothy to the hospital where Anne and the social worker meet up with her.

Because of the assistance coordination network and each its components, Dorothy remains learning new things, able to easily order service, and has access to information through an easily utilized voice interface. Through the assistance coordination network and one or more of its elements, Anne and the social worker have an enhanced capability to monitor Dorothy for her safety and wellbeing. And the hub and/or its associated assistance coordination network has potentially saved Dorothy from serious additional injury or even death.

Although the present embodiments have been described with reference to specific example embodiments, it will be evident that various modifications and changes may be made to these embodiments without departing from the broader spirit and scope of the various embodiments. For example, the various devices, engines, algorithms and modules described herein may be enabled and operated using hardware circuitry (e.g., CMOS based logic circuitry), firmware, software or any combination of hardware, firmware, and software (e.g., embodied in a non-transitory machine-readable medium). For example, the various electrical structure and methods may be embodied using transistors, logic gates, and electrical circuits (e.g., application-specific integrated (ASIC) circuitry and/or Digital Signal Processor (DSP) circuitry).

Each of the memories of the devices (e.g., the memory 203, the memory 303, the memory 403, the memory 503, the memory 603) may be random access memory (RAM), a storage device (e.g., an optical disk, a magnetic disk, a solid-state memory), a volatile memory, a memrister, a solid-state memory, or another type of computer-readable memory capable of storing computer bits).

In addition, it will be appreciated that the various operations, processes and methods disclosed herein may be embodied in a non-transitory machine-readable medium and/or a machine-accessible medium compatible with a data processing system (e.g., the server assistance device 200, the sensing pod 300, the automated assistance server 400, the emergency server 500, the scheduling server 600, the device 700). Accordingly, the specification and drawings are to be regarded in an illustrative rather than a restrictive sense.

The structures and modules in the figures may be shown as distinct and communicating with only a few specific structures and not others. The structures may be merged with each other, may perform overlapping functions, and may communicate with other structures not shown to be connected in the figures. Accordingly, the specification and/or drawings may be regarded in an illustrative rather than a restrictive sense.

In addition, the logic flows depicted in the figures do not require the particular order shown, or sequential order, to achieve desirable results. In addition, other steps may be provided, or steps may be eliminated, from the described flows, and other components may be added to, or removed from, the described systems. Accordingly, other embodiments are within the scope of the preceding disclosure.

What is claimed is:

1. A system comprising:
a speaker for generating a verbal status query to a user;
a microphone to gather from an immediate environment of the microphone at least one of a voice communication of a user and an ambient sound of the immediate environment;
a network interface controller providing communicative coupling to at least one instance of a voice controlled assistance service and at least one instance of an automated emergency assistance service;
at least one processor;
a memory operatively coupled to the at least one processor;
the at least one processor configured to:
generate the verbal status query for the user, responsive to an initiating event;
determine occurrence of an event of concern, based on a response or a non-response event, the non-response event defined as a failure to receive by the microphone a recognizable response from the user;
determine that the event of concern is an emergency event requiring confirmation;
initiate a confirmation request to confirm the emergency event, wherein initiation of the confirmation request includes at least one query for additional information to define the emergency event, and the at least one processor is configured to communicate the at least one query as at least part of the confirmation request; and
execute an emergency action in response to confirmation of the emergency event or a non-response, wherein execution of the emergency action includes two-way communication between a user device and an emergency service.

2. The system of claim 1, wherein in response to identification of the emergency event, the at least one processor is configured to operate as a conference bridge linking any of the user, a caregiver, and an emergency service provider in a common communication channel.

3. The system of claim 1, wherein the at least one processor is configured to select the emergency action based, at least in part, on analyzing the additional information received in response to the at least one query for additional information.

4. The system of claim 1, wherein the at least one processor is configured to identify at least one of a button press, sound, vibration, or presence signal as the initiating event.

5. The system of claim 1, wherein the initiating event is a proactive status request, and the at least one processor is configured to automatically trigger the initiating event based on a user profile.

6. The system of claim 1, wherein the at least one processor is configured to transmit a status query to a device of the user upon occurrence of the event of concern.

7. The system of claim 1, wherein the at least one processor is configured to determine that the event of concern is an emergency event requiring confirmation based, at least in part, on a second non-response event.

8. The system of claim 1, wherein the at least one processor is configured to automatically re-route a destination of a set of voice communications of the user from a first voice controlled assistance service that provides a general assistance to a second voice controlled assistance service comprising an automated emergency assistance service.

9. The system of claim 1, wherein the at least one processor is configured to execute the emergency action based on detection of at least one of a particulate sensor or a chemical sensor.

10. The system of claim 1, wherein the at least one processor is configured to establish a video feed between the emergency service and the user.

11. A computer implemented method for managing emergency services, the method comprising:
generating, by at least one processor, a verbal status query for a user at a speaker, responsive to an initiating event;
determining, by the at least one processor, occurrence of an event of concern, based on a response or a non-response event received by a microphone, the non-response event defined as a failure to receive by the microphone a recognizable response from the user;
determining, by the at least one processor, that the event of concern is an emergency event requiring confirmation;
initiating, by the at least one processor, a confirmation request to confirm the emergency event, wherein initiation of the confirmation request includes at least one query for additional information to define the emergency event, and the at least one processor is configured to communicate the at least one query as at least part of the confirmation request; and
executing, by the at least one processor, an emergency action in response to confirmation of the emergency event or a non-response, wherein execution of the emergency action includes two-way communication between a user device and an emergency service.

12. The method of claim 11, wherein in response to identification of the emergency event, linking any of the user, a caregiver, and an emergency service provider in a conference.

13. The method of claim 11, wherein the method further comprises selecting the emergency action based, at least in part, on analyzing the additional information received in response to the at least one query for additional information.

14. The method of claim 11, wherein the method further comprises identifying at least one of a button press, sound, vibration, or presence signal as the initiating event.

15. The method of claim 11, wherein the initiating event is a proactive status request, and the method further comprises automatically triggering the initiating event based on a user profile.

16. The method of claim 11, wherein the method further comprises transmitting a status query to a device of the user upon occurrence of the event of concern.

17. The method of claim 11, wherein the method further comprises determining that the event of concern is an emergency event requiring confirmation based, at least in part, on a second non-response event.

18. The method of claim 11, wherein the method further comprises automatically re-routing a destination of a set of voice communications of the user from a first voice controlled assistance service that provides a general assistance to a second voice controlled assistance service comprising an automated emergency assistance service.

19. The method of claim 11, wherein the method further comprises executing the emergency action based on detection of at least one of a particulate sensor or a chemical sensor.

20. The method of claim 11, wherein the method further comprises establishing a video feed between the emergency service.

* * * * *